(12) United States Patent
Do Rêgo Filho

(10) Patent No.: US 11,602,481 B2
(45) Date of Patent: Mar. 14, 2023

(54) DRY IMMERSION BED

(71) Applicant: José Fortes Napoleão Do Rêgo Filho, Teresina (BR)

(72) Inventor: José Fortes Napoleão Do Rêgo Filho, Teresina (BR)

( * ) Notice: Subject to any disclaimer, the term of this patent is extended or adjusted under 35 U.S.C. 154(b) by 401 days.

(21) Appl. No.: 16/877,110

(22) Filed: May 18, 2020

(65) Prior Publication Data
US 2021/0128396 A1  May 6, 2021

(30) Foreign Application Priority Data

Nov. 6, 2019 (BR) .......................... 1020190233001

(51) Int. Cl.
| | |
|---|---|
| A61G 7/05 | (2006.01) |
| A61H 9/00 | (2006.01) |
| A61F 7/00 | (2006.01) |
| A61G 7/005 | (2006.01) |
| A61G 7/008 | (2006.01) |
| A61G 7/16 | (2006.01) |

(Continued)

(52) U.S. Cl.
CPC ......... *A61H 9/0028* (2013.01); *A61F 7/0085* (2013.01); *A61G 7/005* (2013.01); *A61G 7/008* (2013.01); *A61G 7/015* (2013.01); *A61G 7/018* (2013.01); *A61G 7/05* (2013.01); *A61G 7/0507* (2013.01); *A61G 7/05784* (2016.11); *A61G 7/065* (2013.01); *A61G 7/16* (2013.01); *A61G 10/02* (2013.01); *A61H 1/001* (2013.01); *A61H 1/008* (2013.01); *A61H 9/0021* (2013.01); *A61F 2007/0086* (2013.01); *A61H 2009/0035* (2013.01); *A61H 2201/0207* (2013.01); *A61H 2201/1654* (2013.01)

(58) Field of Classification Search
CPC ........ A61G 7/005; A61G 7/008; A61G 7/015; A61G 7/018; A61G 7/05; A61G 7/0507; A61G 7/05784; A61G 7/065; A61G 7/16; A61G 10/02; A61H 1/001; A61H 1/008; A61H 9/0021; A61H 2201/0207; A61H 37/005; A61F 2007/0086
See application file for complete search history.

(56) References Cited

U.S. PATENT DOCUMENTS

| | | |
|---|---|---|
| 3,692,028 A | 9/1972 | Etten et al. |
| 2007/0157376 A1* | 7/2007 | Paz .................. A61H 33/02 4/540 |

FOREIGN PATENT DOCUMENTS

WO    2012098076 A1    7/2012

OTHER PUBLICATIONS

Feasibility and Safety of Hydrotherapy in Critically Ill Ventilated Patients; Karin M. Felten-Barentsz, P.T., M.Sc. et al.; American Journal of Respiratory and Critical Care Medicine vol. 191, No. 4, pp. 476-477; Feb. 15, 2015.

(Continued)

*Primary Examiner* — Fredrick C Conley
(74) *Attorney, Agent, or Firm* — Avek IP, LLC; Kent R. Erickson

(57) ABSTRACT

The dry-immersion bed of the present invention is suitable for intensive care units (ICUs) and fulfills the function of providing treatment for diseases such as capillary leak syndrome. The dry immersion bed fulfills the function of recovering cardiovascular physiology by normalizing the systemic distribution of water, albumin and electrolytes, and improving lymphatic drainage, venous return, cardiac output, cell metabolism and immunity.

34 Claims, 19 Drawing Sheets

(51) Int. Cl.
    *A61G 7/015*     (2006.01)
    *A61G 7/018*     (2006.01)
    *A61G 7/057*     (2006.01)
    *A61G 7/065*     (2006.01)
    *A61G 10/02*     (2006.01)
    *A61H 1/00*     (2006.01)

(56) References Cited

OTHER PUBLICATIONS

Immersion-enhanced fluid redistribution can prevent intradialytic hypotension: A prospective, randomized, crossover clinical trial: Correcting redistribution for IDH prevention; Keren Doenyas-Barak et al; International Society for Hemodialysis, pp. 1-6, Feb. 2018.

\* cited by examiner

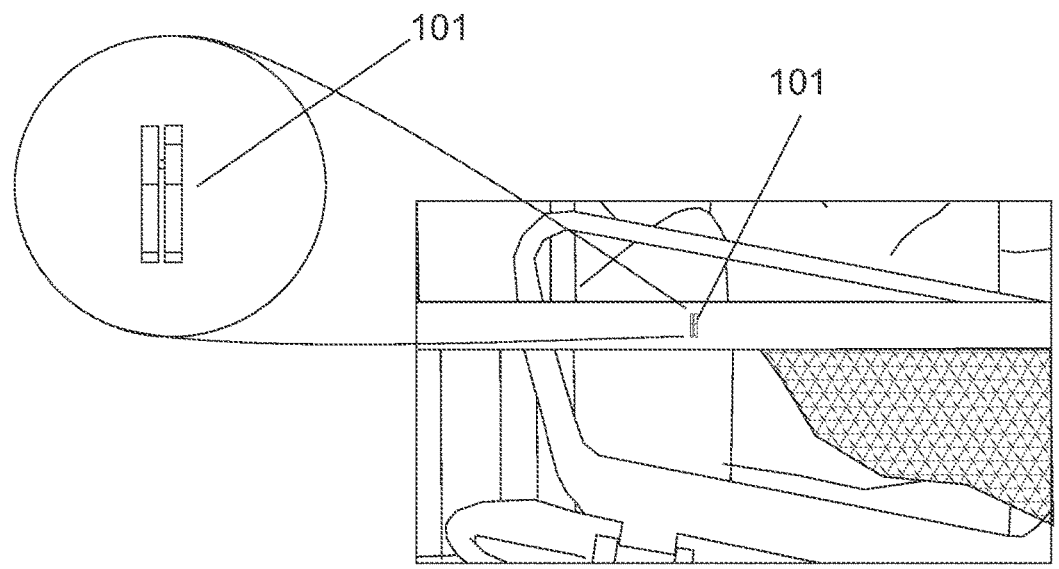
FIG 30
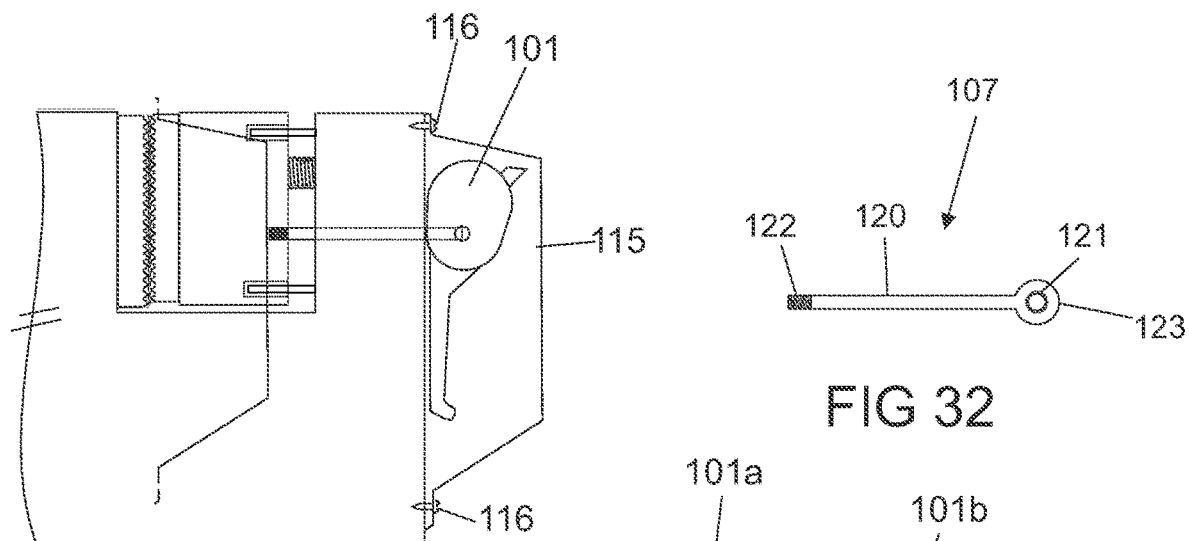
FIG 31
FIG 32
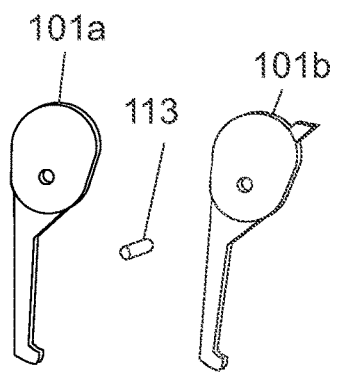
FIG 33

DRY IMMERSION BED

This application claims priority from Brazilian Application BR1020190233001, filed Nov. 6, 2019, the disclosure of which is hereby incorporated herein in its entirety by reference.

FIELD OF THE INVENTION

The invention relates to a dry immersion bed intended for intensive care units (ICUs) and emergency rooms aiming at prevention and treatment of capillary leakage, edema, lymph accumulation and venous stasis in critically ill patients.

BACKGROUND OF THE INVENTION

Capillary leak syndrome is a disease characterized by increased permeability of capillary endothelial cells, allowing fluid leakage from the circulatory system into the interstitial fluid.

Sepsis is the disease most commonly associated with capillary leak syndrome, but many other diseases can present endothelial dysfunction. Sepsis is associated with endothelial cells dysfunction, leading to hemostasis dysregulation and vascular reactivity, in addition to tissue edema. When the vessels are damaged, the porosity of the capillary walls increases and, consequently, the liquid filtration increases. The lining of endothelial cells in capillary vessel is a unique cellular system that provides the interface between blood and parenchyma cells responsible for organ function. Any failure in the endothelial cell implies an increase in microvascular permeability and capillary leakage, which, in turn, result in interstitial fluid accumulation, protein loss and tissue edema.

This makes sepsis one of the major causes concerning appearance of edema in patients with acute illnesses.

Sepsis is a fatal organ dysfunction caused by the host's unregulated response to infection. If not detected at an early stage and readily treated, it can lead to septic shock, multiple organ failure and death. Treatment of patients suffering from sepsis is mostly performed at ICUs. Mortality from sepsis varies from 30 to 50% of the cases. Despite decades of intense research, only a few new therapies have been developed, and the major treatment alternatives are still antibiotic usage, fluid resuscitation and the physiological support for failed biological systems. In fact, sepsis has been described as the "graveyard" of pharmaceutical discoveries because most drugs that seemed promising during in vitro and animal models have been shown to be ineffective in humans.

It is difficult to determine precisely the global epidemiological burden of sepsis. It is estimated that more than 30 million people are affected worldwide each year, potentially leading to 6 million deaths (World Health Organization, Health Topics, Sepsis, 19 Apr. 2018). In Brazil, there are 600,000 new cases of sepsis annually (Glauco Adrieno Westphal; Characteristics and outcomes of patients with community-acquired and hospital-acquired sepsis—2019). Sepsis impact is likely to be greatest in low-income and middle-income countries. One out of ten deaths associated with pregnancy and childbirth is due to maternal sepsis, among which more than 95% of deaths from maternal sepsis belonging to low- and middle-income countries. It is estimated that 3 million newborns and 1.2 million children suffer from sepsis globally each year (World Health Organization, Health Topics, Sepsis, Apr. 19, 2018).

The estimated cost associated with only one adult case of sepsis is USD 38,000 in the United States (JihaneHajj—The "Centrality of Sepsis"—2018), USD 26,000 to USD 32,000 in Europe and around USD 10,595 in Brazil (Maynara Barreto—Sepsis in a university hospital—2016).

In addition to sepsis, other diseases that can lead to capillary leak syndrome are: trauma, hemorrhage, burns, acute pancreatitis, Clarkson's disease, graft syndrome, differentiation syndrome, ovarian hyperstimulation syndrome, hemophagocytolinfohistiocytosis, viral hemorrhagic fevers, autoimmune diseases, snakebite poisoning and ricin poisoning. In addition to these diseases, it is known that some patients may have capillary leak syndrome as a side effect in the administration of some drugs.

In the medical literature, there is a consensus that there are not any effective treatments for capillary leak syndrome. (Eric Siddall—Capillary leak syndrome—2017)

In the last decades, many clinical trials have tested immunomodulatory compounds designed to restore homeostasis in patients with sepsis. Despite these efforts, which cost hundreds of millions of dollars, not a single new drug has been integrated into clinical practice. Thus, it is obvious that the clinical and scientific communities need to reconsider the therapeutic approach to sepsis. New strategies to treat sepsis face serious challenges along their way to patient's treatment in the Intensive Care Unit (Tom van der Poll—Future of sepsis therapies 2016).

Under normal conditions, several factors control the interstitial fluid flow direction, including hydrostatic pressure, oncotic pressure, endothelial integrity as well as the lymphatic system. These factors are believed to be guided by Starling's law, which describes the movement of fluids through capillaries being proportional to capillary permeability, differences in transcapillary hydrostatic pressure and differences in transcapillary oncotic pressure. The Starling's law equation is: Filtration=$K_f \times (P_c - P_{if} - O_c + O_{if})$. Where $P_c$ is the hydrostatic capillary pressure, $P_{if}$ is the hydrostatic pressure of the interstitial fluid, $O_c$ is the plasma colloidosmotic pressure, $O_{if}$ is the colloidosmotic pressure of the interstitial fluid and $K_f$ is the capillary filtration coefficient (permeability×surface area).

Capillary pressure forces the fluid from capillaries into the interstice. The pressure of the interstitial fluid has negative values and the fluid is forced into the interstice. The plasma oncotic pressure exerts an osmotic effect through the capillary walls, forcing the fluid into the intravascular space. Interstitial oncotic pressure forces some fluid out of the capillary walls. Typical capillary pressure values varies between 32 and 36 mmHg. In subcutaneous tissues, interstitial pressure tends to be slightly negative. On average, the interstitial pressure is approximately −6 mmHg. The capillary coloidosmotic pressure of an average capillary is about 28 mmHg. It has the opposite effect to both hydrostatic blood pressure that pushes water and small molecules out of the blood into the interstitial spaces, and interstitial coloidosmotic pressure.

These factors determine the balance of the body's extracellular water division between blood plasma and regions outside the bloodstream. Significant capillary leakage in critical cases most often implies an increased capillary permeability, the most common cause of edema in critically ill patients.

Edemas rarely arise from small changes in hemodynamic forces. To be more precise, some studies have identified that an increase of 15 mmHg in the gradient in favor of the filtration is necessary (flow from the intravascular medium to the interstitial space) in order to cause edema appearance.

Edemas, therefore, arise when there is an excessive volume of interstitial fluid, characterizing the clinical profile of edemas. Thus, a mechanical approach to the treatment of edema and capillary leakage is necessary. It would be interesting to apply positive external pressure onto the human body to prevent capillary leakage and to stimulate the return of accumulated fluid in the interstitial space (edema) into the intravascular environment.

BRIEF DESCRIPTION OF PREVIOUS INVENTIONS

Hyperbaric chamber: until now, the application of positive external pressure onto the patient's body for therapeutic purposes has been performed in a very artisanal manner. One approach consists in positioning the patient in a hyperbaric chamber. Because the chamber is a closed environment, it is difficult to install and remove a critically ill patient. The enclosed environment also prevents easy and regular patient handling and the external pressure applied is uniform throughout the body surface exposed to pressure, not allowing for pressure reduction along the caudal-cranial axis. Moreover, the hyperbaric chamber is unsuitable for emergency procedures.

Pneumatic compression: peripheral manipulation of interstitial pressure, with intermittent pneumatic compression devices and graduated compression stockings may be beneficial, but these devices contribute exclusively for pressure application onto the legs and thighs, therefore being ineffective.

Water immersion: some ICUs use water immersion as a hydrotherapy approach. In these ICUs there is a dedicated swimming pool with a movable floor. Ventilated patients (with artificial respiration devices) admitted to the medical, surgical or thoracic ICU are eligible for hydrotherapy if they are severely weak and able to respond to verbal commands. Before hydrotherapy, any central venous catheters (internal jugular vein) and arterial catheters (radial artery) are disconnected and covered with a transparent dressing and fixed with an elastic bandage. During transfer and hydrotherapy, patients are ventilated with a portable ventilator, using pressure support mode. Pulse oximetry and heart rate are monitored in these cases using a portable clip device during transport and during hydrotherapy; the pulse oximeter is used only when necessary, based on clinical judgment. The mobility team includes two ICU nurses, a physical therapist and a doctor. The total duration of the hydrotherapy session is approximately 60 minutes, including briefing, transport to the pool, patient preparation by the pool, hydrotherapy, bathing and transport back to the ICU. In this hydrotherapy model, the patient gets wet. (Karin M. Felten-Barentsz, Antonius J. C. Haans, Arthur S. Slutsky, Leo M. A. Heunks. American Journal of Respiratory and Critical Medicine Volume 191 Number 4|Feb. 15, 2015).

This hydrotherapy model is performed outside the ICU, is wet and has no structure to provide safety, mobility and comfort to the patients during their stay in the ICU.

Head out water immersion (HOWI) during hemodialysis: Intradialytic hypotension (IDH) is an important cause of morbidity and mortality among patients on hemodialysis. In a hemodialysis unit, Head out of water immersion (HOWI) is applied on patients with intradialytic hypotension (IDH). Head out water immersion (HOWI) applies positive pressure in the interstitial space and displaces water from the interstitial space to the intravascular space. Immersion in water with the head out during dialysis facilitates the filling of the interstitial space towards the intravascular space, and can, thus, prevent IDH associated with delayed circulatory replenishment. An 800 liters jacuzzi bath is used for immersion. The bath is filled with purified water, which is heated to a physiological temperature of 34 to 35° C., before each hemodialysis session. The water is recirculated using a thermostat and heating device to maintain a constant temperature. Patients enter the bath and sit upright for 15 minutes before dialysis. During the session, blood pressure and heart rate are measured every 15 minutes using the conventional sphygmomanometer. Although the water immersion method is considered a powerful tool for water redistribution, it has substantial negative effects on dialysis and ultrafiltration tolerance, also requiring installation of special equipment, recruitment of personnel for patient immersion and removal from the pool water and consultation regarding infection control. Thus, for most patients, immersion cannot be routinely used. The immersion procedure is safe and no side effects were reported during wet sessions. This is the first study to show that effective interventions aimed at facilitating the filling during hemodialysis may prevent IDH (Keren DOENYAS-BARAK, Nedal GARRA, Ilia BEBERASHVILI, Shai EFRATI).

Increased liquid redistribution by immersion may prevent intradialytic hypotension: A prospective, randomized, crossover clinical trial—Hemodialysis International 2018; 00: 00-00, DOI: 10.1111/hdi.12634. This method, as described here, is impractical to be performed in an ICU, because the 800 L jacuzzi occupies a large physical space and the method also requires wet immersion.

WO 2012/098076 AI: the equipment disclosed in WO 2012/098076 AI is not intended to be used in intensive and emergency care units for an acute or prolonged period during hospitalization of patients. This equipment is more specifically intended to create a weightless environment and may be useful for the treatment of various diseases in patients outside the ICUs and Emergency Units.

Nevertheless, this previous technique:
(i) does not comprise a mattress to comfortably support the patient, especially when the bed is not under fluid immersion liquid;
(ii) does not comprise four angularly adjustable bed portions capable of providing different therapeutic treatment positions;
(iii) does not allow movements of Trendelenburg position, reverse Trendelenburg position, elevation of the back and legs, lateral positions and anti-shock position;
(iv) does not include movements of bed retraction and extension, nor does it describe electrical control of such movements;
(v) does not include a device that enables rapid conversion to a cardiopulmonary resuscitation position;
(vi) does not comprise a tunnel (21) for X-ray cassette (22), mounted under the backrest segment enabling x-ray image procedures in a sitting position;
(vii) does not include CPR (Cardio-Pulmonary Resuscitation) function in the back and thighs support sections. The "CPR Control" function consists in lowering the head and knee portions and raising the foot portion. The use of a CPR plate may increase cardiopulmonary resuscitation effectiveness;
(viii) the grid or platform does not allow for lateral movements (lateral inclinations) which are essential for respiratory physiotherapy;
(ix) does not include removable headboard, removable pad, or wired hand controller;
(x) does not include supports with hooks for drainage bags on the sides;
(xi) does not have a control system equipped with a battery;

(xii) does not have a control device for anti-shock position—bed structure with all segments leveled in the Trendelenburg position;
(xiii) does not include side rails and control device to facilitate four side rails lifting (2 on each side);
(xiv) does not enable bed usage in any of the three chair positions: Dining Chair, Full Chair and Chair Exit;
(xv) does not include nurse calling device;
(xvi) does not include a bed battery;
(xvii) does not include a control device for light adjustment of the bedside and tank portions; among other drawbacks.

U.S. Pat. No. 3,692,028 reveals a treatment tank for emergency burns victims.

The U.S. Pat. No. 3,692,028 tank was specifically designed for emergency treatment of acute burns victims. The present device was developed in relation to the treatment of burns on human bodies. It is suitable for use in hospital emergency rooms, industrial first aid stations or similar places where burn victims may be readily treated after the injury. Immediate cooling of the skin under controlled conditions in a liquid bath can often decrease the skin damage severity. Effective emergency cooling of the patient's skin requires almost complete body immersion.

This equipment comprises an open rectangular enclosure filled with liquid and a movable articulated patient support platform inside the enclosure, together with means to selectively stop the movement of some portions of the platform, allowing the articulation of the rest of the platform.

The tank comprises an open casing with a substantially rectangular cross-section. It consists of two parallel side walls, spaced transversely from each other and opposite end walls.

The platform is articulated in order to allow adjustment according to patient's desire. The patient can be kept in the liquid for up to two hours. This equipment is not intended for use in ICUs for the reasons specified below:
(i) does not include mattress to comfortably support the patient, especially when the bed is not under liquid immersion;
(ii) does not include an X-ray cassette tunnel, mounted under the backrest segment for X-ray image procedures in a sitting position;
(ii) does not include a panic button to call nurses;
(iii) does not include a bed battery;
(iv) does not include control device for light adjustment of the bedside and tank portions;
(v) does not include movements of bed retraction and extension, nor does it describe electrical control of such movements;
(vi) does not include robust and fast electric actuators or elevators that make movements more precise and faster in emergency situations;
(vii) does not include a specific hose for physiotherapy in the lungs by means of water jets;
(viii) does not include a hydrotherapy treadmill on the tank floor for early mobility;
(ix) does not include transparent side walls, which allow for complete visibility of the patient's body;
(x) does not include a pressure gauge in its structure. In this sense, it should be noted that the measurement and monitoring of hydrostatic pressure is of fundamental importance, as it guarantees the correct control of the mentioned changes, which are of great relevance for the present equipment, without causing major complications to the patient, such as hampering peripheral blood circulation due to long period application of hydrostatic pressure considered higher than the tissue perfusion pressure;
(x) the bed does not include waterproof elastic fabric cover, side rails, and support with hooks for drainage bags on the sides;
(xi) does not include CPR (cardio-pulmonary resuscitation) function; among other drawbacks.

Therefore, it is necessary to develop an equipment that aims to create conditions in intensive care units (ICUs) to provide the application of positive external pressure onto the body of critically ill patients with capillary leakage, edema, lymph accumulation and venous blood accumulation in the peripheral circulatory system.

OBJECTIVES OF THE INVENTION

The present invention provides an equipment capable of preventing liquid and protein leakage into the interstitial space.

Another objective is the displacement of the accumulated blood and lymph in the peripheral venous system and interstitial space, respectively, to the circulatory system, normalizing the distribution of the circulating blood volume and significantly improving immunological response.

The present invention also provides an equipment capable of exerting controlled pressure over the entire patient epidermis, being able to apply a decreasing pressure in the caudal-cranial axis (from the feet to the head). The invention also aims to significantly improve respiratory physiotherapy with the application of chest vibration and percussion effects, also optimizing the application of the PRONA position rapidly.

Another objective is the implementation of early physical mobility through therapy on a treadmill without getting out of bed, in addition to the prevention of bed sores (pressure ulcers).

Additionally, the present invention provides equipment that permits the hemodialysis session to be carried out in Intensive Care Units under dry immersion conditions.

Another objective is to provide an equipment design that is easy to operate, requiring simple maintenance and little extra space in the ICU.

Another objective is to provide a treatment of pathologies such as: edema syndrome (the oedema syndrome), liver cirrhosis, glomerulonephritis; glomerulopathies, hypertonic disease in stages I-II; hypertonic-type neuro-circulatory dystonia; neuroses; degenerative dystrophic diseases of the locomotor system; peptic ulcers, dyskinesia of the gastrointestinal tract; reflective tonic disorders; somatoform dysfunction of the vegetative nervous system; condition after a blood circulation disorder in the brain; ischemic stroke, consequences of infantile cerebral palsy, including infantile cerebral palsy itself; hypertonic disease; varicose expansion of the veins, stage 1-2; spinal diseases involving neurological symptoms with stages of pain syndrome 1-2; chronic fatigue syndrome; sleep disorders; conditions after suffering myocardial infarction; portal hypertension; conditions after alcoholic intoxication—abstinent syndrome, pregnancy, burns, erysipelas, hyperthermia, hypothermia, compartmental syndromes, arterial hypertension.

BRIEF DESCRIPTION OF THE INVENTION

The invention consists of a dry immersion bed for treating patients, which comprises: a membrane, a water tank with a floor and four walls and a bed. The four walls and the floor of the water tank form an open top water-tight container. The membrane is arranged between the patient and the external surface of the bed, separating the patient from the water below him.

The bed is capable of displaying, at least, the following degrees of freedom in relation to the water tank floor: up and down in relation to the floor; tilted forward and tilted backwards in relation to the front and rear wall; right rotation and left rotation towards the side walls; chair position and lying position.

The bed is connected to the tank's floor using at least one vertical actuator; and is segmented into four platforms, which are: first platform; second platform; third platform; and the fourth platform; the first platform being adapted to support the patient's head and back; the second platform being adapted to support the patient's seat (buttocks); the third platform being adapted to support the patient's thighs; and the fourth platform being adapted to support the patient's legs and feet.

The platforms are (preferably) perforated and have degrees of freedom between themselves and are equipped with angular actuators, capable of providing a change in the angle defined between the different platform portions (meaning: the angle defined between the first and second platforms; the angle defined between second and third platforms; and the angle defined between the third and fourth platforms).

The vertical actuators together with the angular actuators, being able to provide the following treatment positions: fowler position; semi-fowler position; trendelenburg position; anti-trendelenburg or reverse trendelenburg position; cardiac position; anti-shock position; and inclination with head position above the feet.

For the purpose of treatment for several days in ICUs, in which the patient alternates moments out of the water with moments of immersion, it is necessary to use a mattress, preferably inflatable, to comfortably accommodate the patient. In addition, it is important that the mattress is perforated, to allow water to circulate, and made of salty water resistant material (e.g. elastomer, or polychloroprene), as it may be necessary to add salt (NaCl) to increase the density of water in periods of immersion. Additionally, it is important that the water temperature is set as close to normal body temperature (36.5° C.), as ICUs are normally very cold. In addition, hyperthermia and/or hypothermia are a common occurrence, enforcing the need for water temperature control.

In order to provide the bed structure with greater safety against shocks, internal pressure and for better fixation of the transparent walls, the edges and floor of the tank are made of stainless steel, austenitic or duplex type. The combination of these characteristics allows for safe use of the equipment also assuring it is adapted to ICU conditions for several days.

BRIEF DESCRIPTION OF THE DRAWINGS

FIG. 1 is a front view of a dry immersion bed mounted within a water tank and intended for ICU usage according to the present invention with the bed, having a patient supported thereon, tilted towards a health professional;

FIG. 2 is a front view of the dry immersion bed intended for ICU usage according to the present invention with the bed tilted away from a health professional;

FIG. 3 is a perspective view of the dry immersion bed intended for ICU usage according to the present invention with the bed in parallel with the horizontal edges of the water tank;

FIG. 4 is a perspective view of the dry immersion bed intended for ICU usage according to the present invention with the bed slightly tilted in order to keep the patient's head higher than the patient's feet;

FIG. 5 is a side view of the dry immersion bed with the bed extending parallel with the horizontal edges of the water tank;

FIG. 6 is a side view of the dry immersion bed of the invention with the bed in a chair position.

FIG. 7 is a side view of the dry immersion bed according to the present invention with the bed in a chair position with elevated leg support;

FIG. 8 is a side view of the dry immersion bed according to the present invention with bed in a chair position and the water tank partially filled;

FIG. 9 is a side view of the dry immersion bed according to the present invention with the bed in an extended and inclined position (with the patient's head above the feet), with the water tank fully filled and a waterproof membrane shown positioned between the patient and the bed;

FIG. 10 is a side view of the dry immersion bed according to the present invention with the bed in an extended and inclined position with the patient floating dry at the interface between the waterproof membrane and the tank water;

FIG. 11 is side view of the dry immersion bed according to the present invention with bed in an extended and inclined position with the patient floating dry at the interface between the waterproof membrane and the tank water, with arrows representing the pressure gradient exerted against the patient's dermis;

FIG. 12 is a side view in perspective of the dry immersion bed intended for ICU usage according to the present invention with the bed extending flat and retracted against the floor of the tank, and the patient floating on the membrane that separates the water from the external environment;

FIG. 13 is a front view of the dry immersion bed intended for ICU usage according to the present invention with tank completely filled with water, the bed extending flat and supported against the floor in a retracted position and the patient floating on the waterproof membrane in a position that promotes a pressure gradient with peak pressure on the feet and less pressure on the patient's head;

FIG. 14 is a perspective side view of the water tank according to the present invention as shown in FIGS. 12 and 13 with the healthcare professional holding a hydrostatic pressure hose against the patient's back;

FIG. 15 is a side view of the water tank according to the present invention as shown in FIGS. 12-14 with the healthcare professional holding a hydrostatic pressure hose against the patient's back;

FIG. 16 is a side view of the dry immersion bed according to the present invention with the bed tilted in order to raise the patient's head in relation to the patient's feet and the tank completely filled with water;

FIG. 17 is a side view of the dry immersion bed according to the present invention with the patient being prepared for physical therapy on a treadmill on the bottom of the tank;

FIG. 18 is a side view of the preferred configuration of the dry immersion bed according to the present invention;

FIG. 19 is a top perspective view of the preferred configuration of the dry immersion bed according to the present invention;

FIG. 20 is a perspective view of the preferred configuration of the dry immersion according to the present invention;

FIG. 21 is a perspective view of the preferred configuration of the dry immersion bed according to the present invention with the bed in a sitting position and a third portion of the bed extending parallel to the bed floor;

FIG. 22 is a perspective view of the preferred configuration of the dry immersion bed according to the present invention with the bed in a sitting position and the third portion of the bed positioned obliquely in relation to the bed floor;

FIG. 23 is a perspective view of the preferred configuration of the dry immersion bed according to the present invention with the bed in a horizontal position;

FIG. 24 is a perspective view of a tunnel for an X-ray cassette, mounted under a backrest segment of the bed enabling X-ray image procedures in the sitting position;

FIG. 25 is a perspective view of the preferred configuration of the dry immersion bed according to the present invention with the bed in a sitting position and the third portion of the bed positioned vertically in relation to the bed floor and patient performing exercises on the ergonomic treadmill;

FIG. 26 is a perspective view of the preferred configuration of the dry immersion bed according to the present invention with patient performing exercises on the ergonomic treadmill;

FIG. 27 is an enlarged, perspective view of the preferred configuration of the dry immersion bed showing a hydromassage hose of the dry immersion bed according to the present invention;

FIGS. 28 to 35 reveal different configurations and details comprised by the gripping device;

FIG. 28 is a cross-sectional view of a preferred embodiment of a gripping device for gripping the waterproof membrane.

FIG. 30 is a front view of the lever of the gripping device installed on the immersion bed;

FIG. 31 is a cross-sectional view of a second embodiment of the gripping device including a lid for retaining the lever in a closed position;

FIG. 32 is a side view of a transmission pin of the gripping device;

FIG. 33 is an exploded view of the lever of the gripping device;

FIG. 34 is a fragmentary, perspective view of the gripping device; and

FIG. 35 is a cross sectional view of an alternative configuration for the gripping device.

DETAILED DESCRIPTION OF THE DRAWINGS

Water applies a pressure of 22.4 mmHg/foot, which translates to 1 mmHg/1.36 cm (0.54 inches).

The water tank (2) in which a dry immersion bed (1), (1') is mounted has a depth of at least 30 cm, preferably one meter, therefore, the hydrostatic pressure inside the tank (2) varies from 1 to 74.66 mmHg, from the surface to the bottom. This pressure external to the human body also acts in the interstitial and intracellular space, increasing fluids and lymph drainage through the lymphatic and circulatory systems and correcting the edema. External hydrostatic pressure also compresses the peripheral venous system and displaces the accumulated venous blood into the central circulation.

In addition to these benefits, another functionality of the hydrostatic pressure is the displacement of blood and lymph accumulated in the venous and lymphatic systems to the arterial system, normalizing the circulatory volume distribution.

The application of positive external pressure to the human body is transmitted to the extravascular space, making capillary leakage difficult and, when the external pressure is higher than capillary pressure, promoting the liquid displacement from the interstitial to the intravascular space, and also increasing systemic blood flow and peripheral venous and lymphatic drainage.

Figure 13:
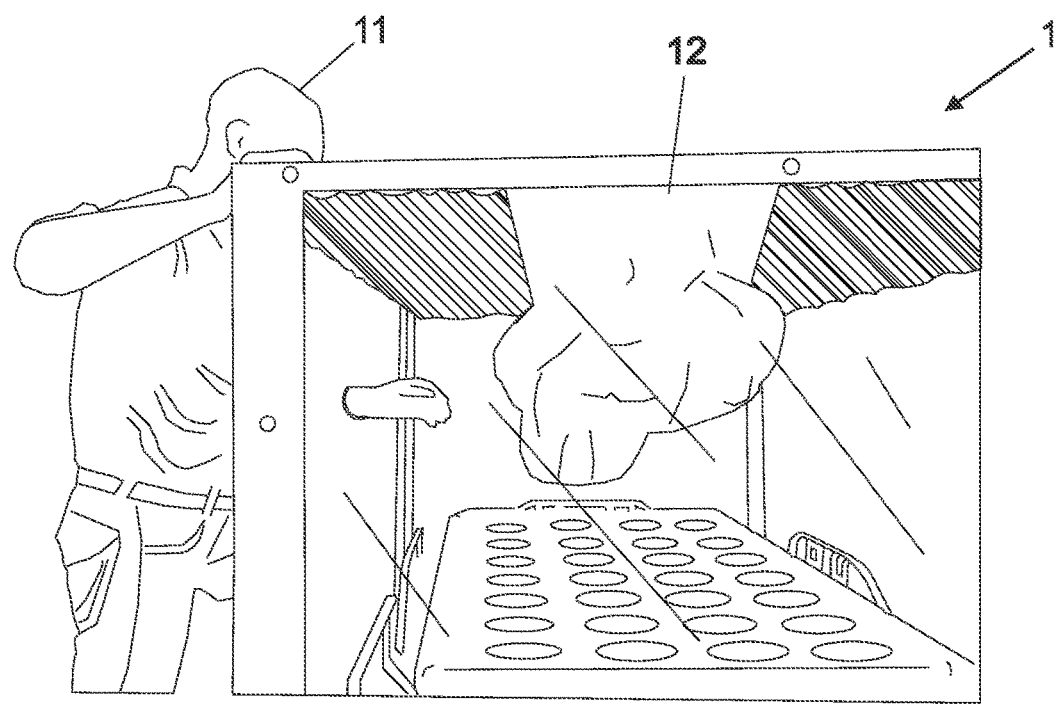
Figure 14:
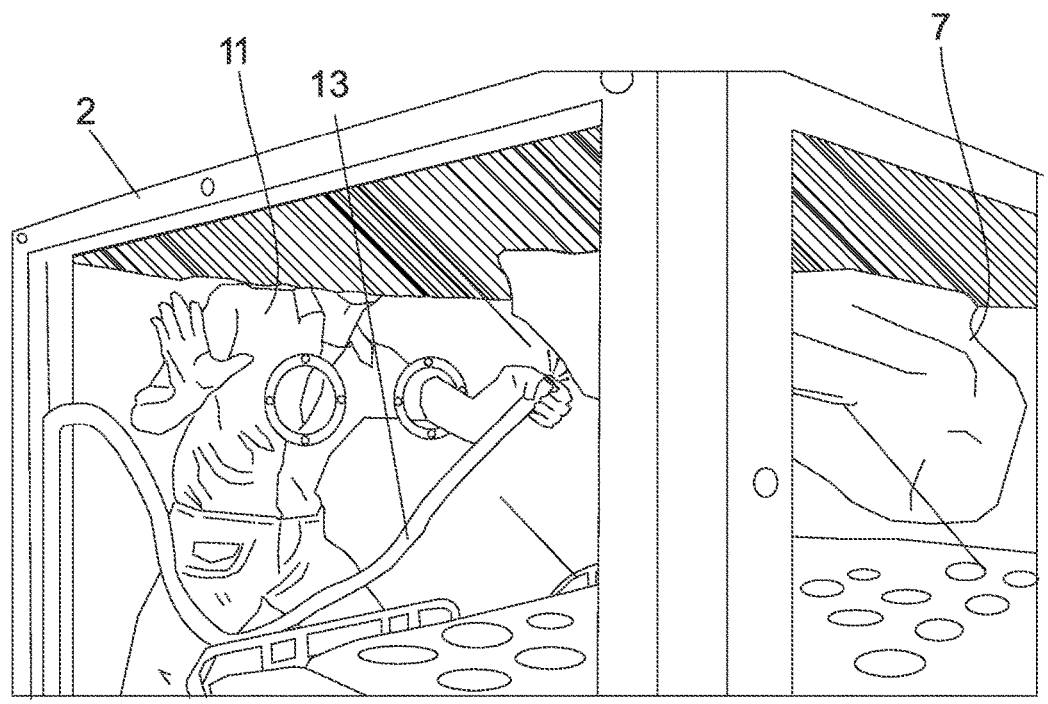
Figure 15:
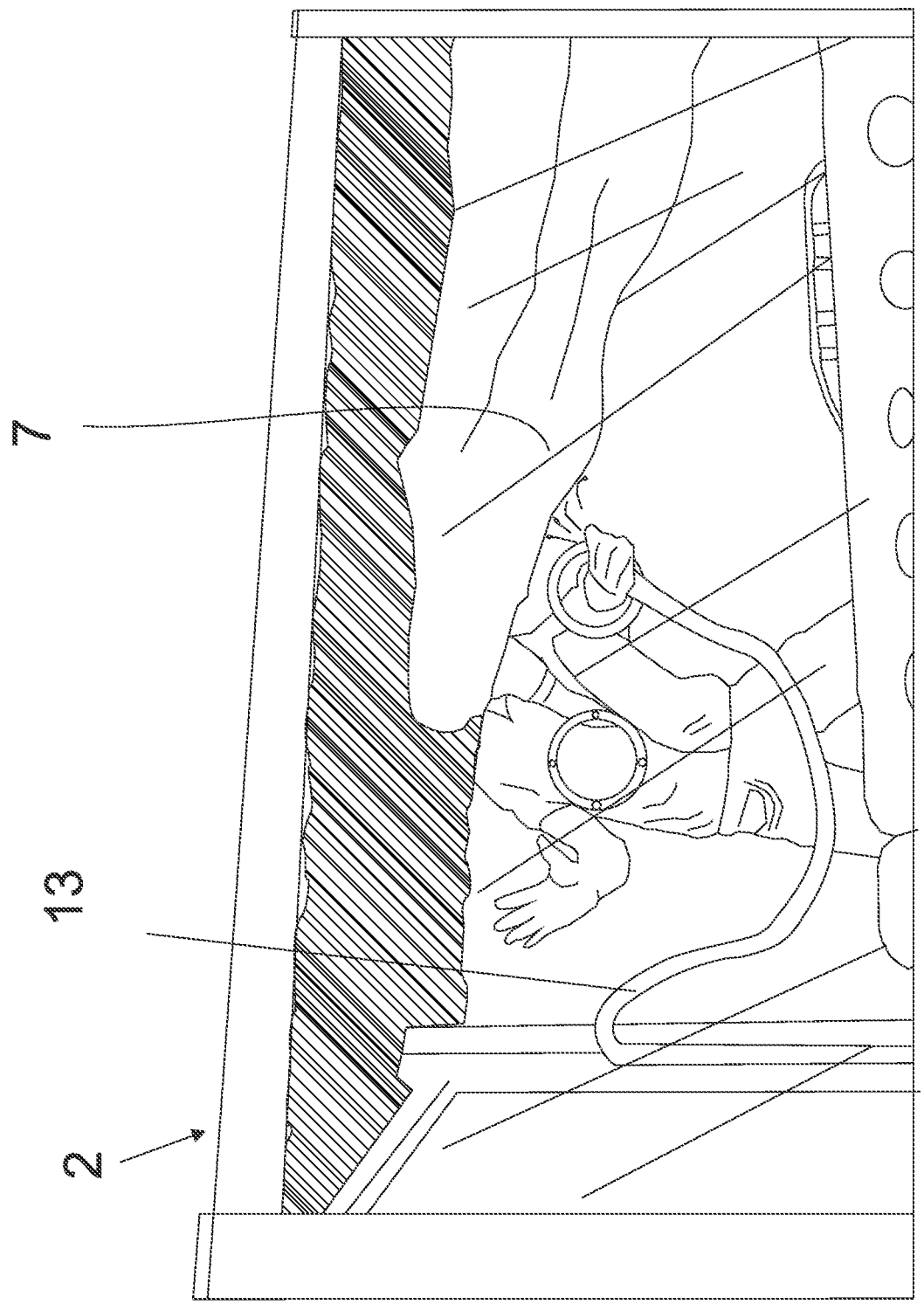
Figure 27:
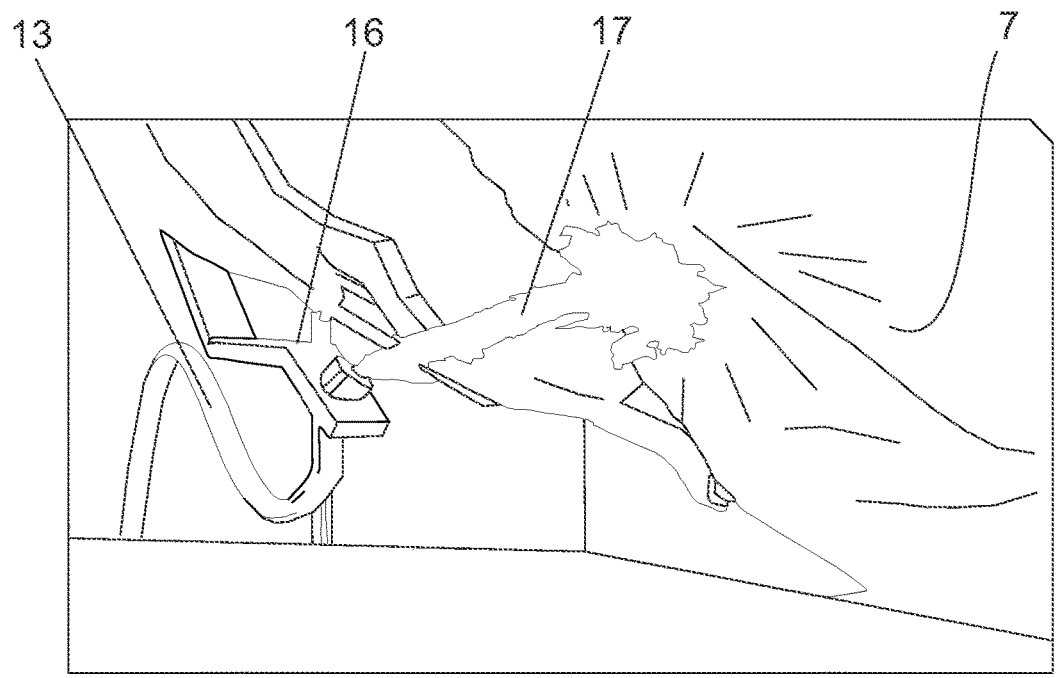

In order to increase the efficiency of respiratory physiotherapy, tank (2) comprises a hydromassage hose (13) (see FIGS. 13, 14 and 27) which, through the emission of water jets, promotes simultaneous vibration and percussion effects on the lungs, facilitating secretions drainage. FIG. 27 shows the preferred configuration of the hydromassage hose (13), which comprises a metallic support (16) anchored in one of the side walls (9'''), (9'''') and equipped with a nozzle capable of propelling a pressurized water jet (17) through its structure.

Short-term dry immersion is easy to apply and therapeutically effective. It may also be beneficial as a method of relaxation. As stated, the water exerts a pressure of 22.4 mmHg/foot, which translates to 1 mmHg/1.36 cm (0.54 inches). In tank (2) with water from this therapeutic equipment of dry immersion, with a preferable depth of at least 01 meter, the hydrostatic pressure varies from 01 to at least 74.66 mmHg, from the surface to the bottom, respectively.

Alternatively, instead of water, tank (2) may be filled with: salt water (water with NaCl); silicone; water with liquid densifiers or a mixture of organic and/or synthetic oils. The presence of solutions other than pure water is important to allow greater hydrostatic pressure control of the fluid inside the tank (2). The presence of silicone droplets in the water may not only increase the hydrostatic pressure, but may also allow a longer life span of the membrane (7), due to the fact that silicone is commonly used as a maintenance lubricant for all sorts of rubber like membranes.

The present invention describes the first dry immersion bed (1) adapted to ICU (intensive care unit) environment and to the medical treatment of patients in the ICU.

From a technical point of view, the pressure to be applied must be evenly distributed over the body surface and can be gradually distributed, the pressure applied onto the chest area being smaller than the one applied onto the feet.

Figure 9:
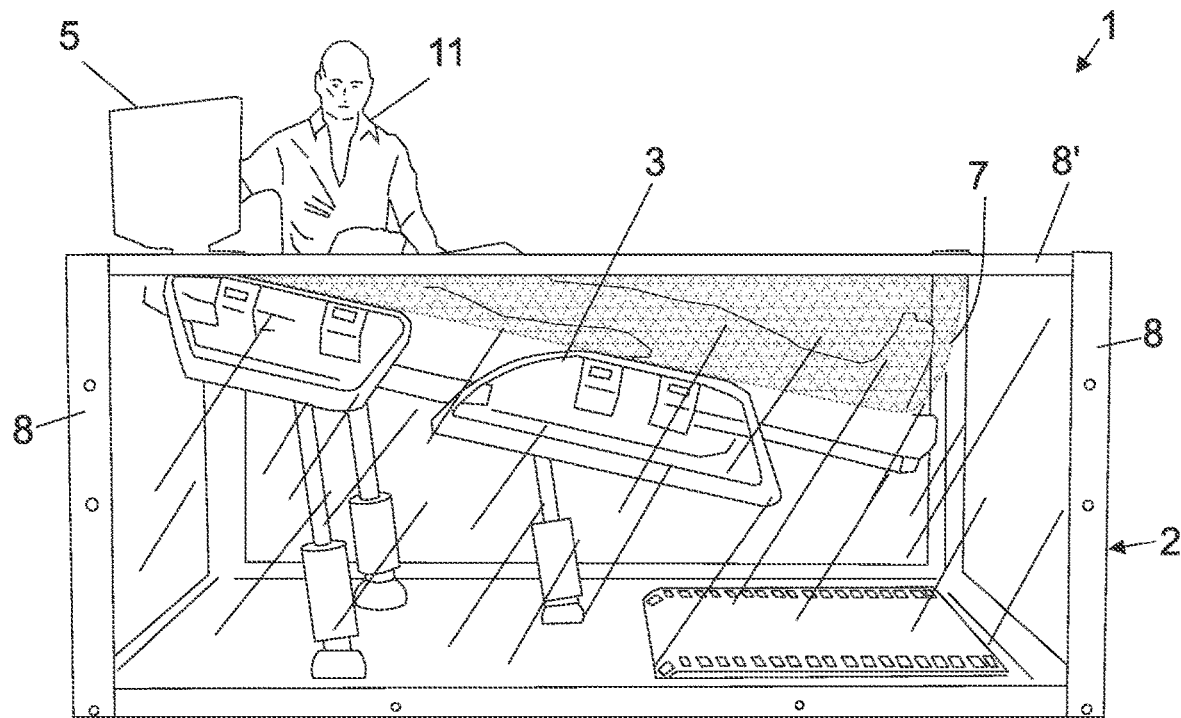
Figure 10:
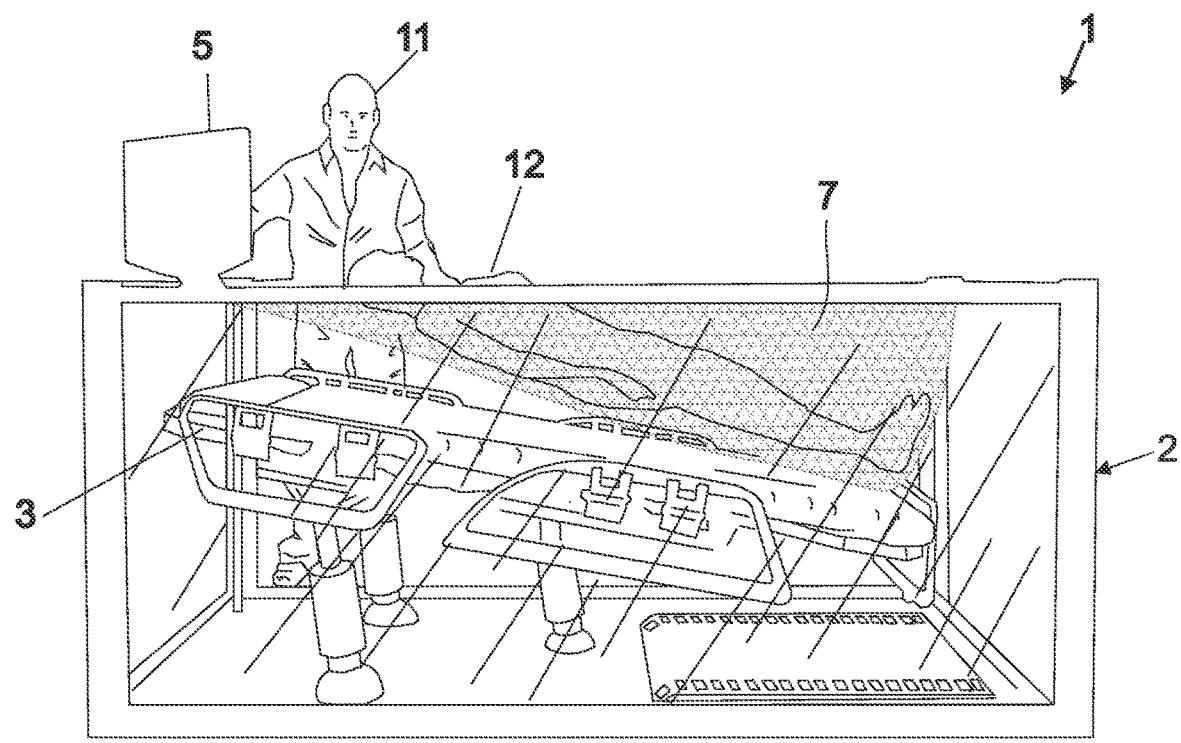
Figure 11:
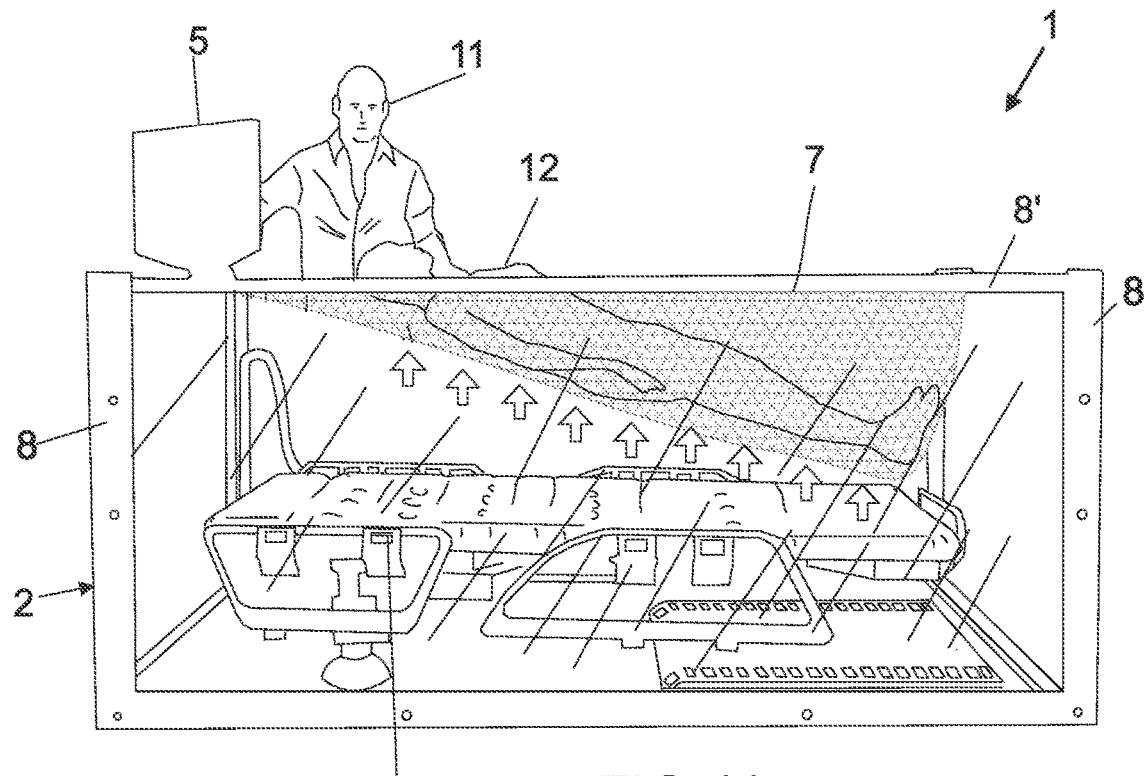
Figure 12:
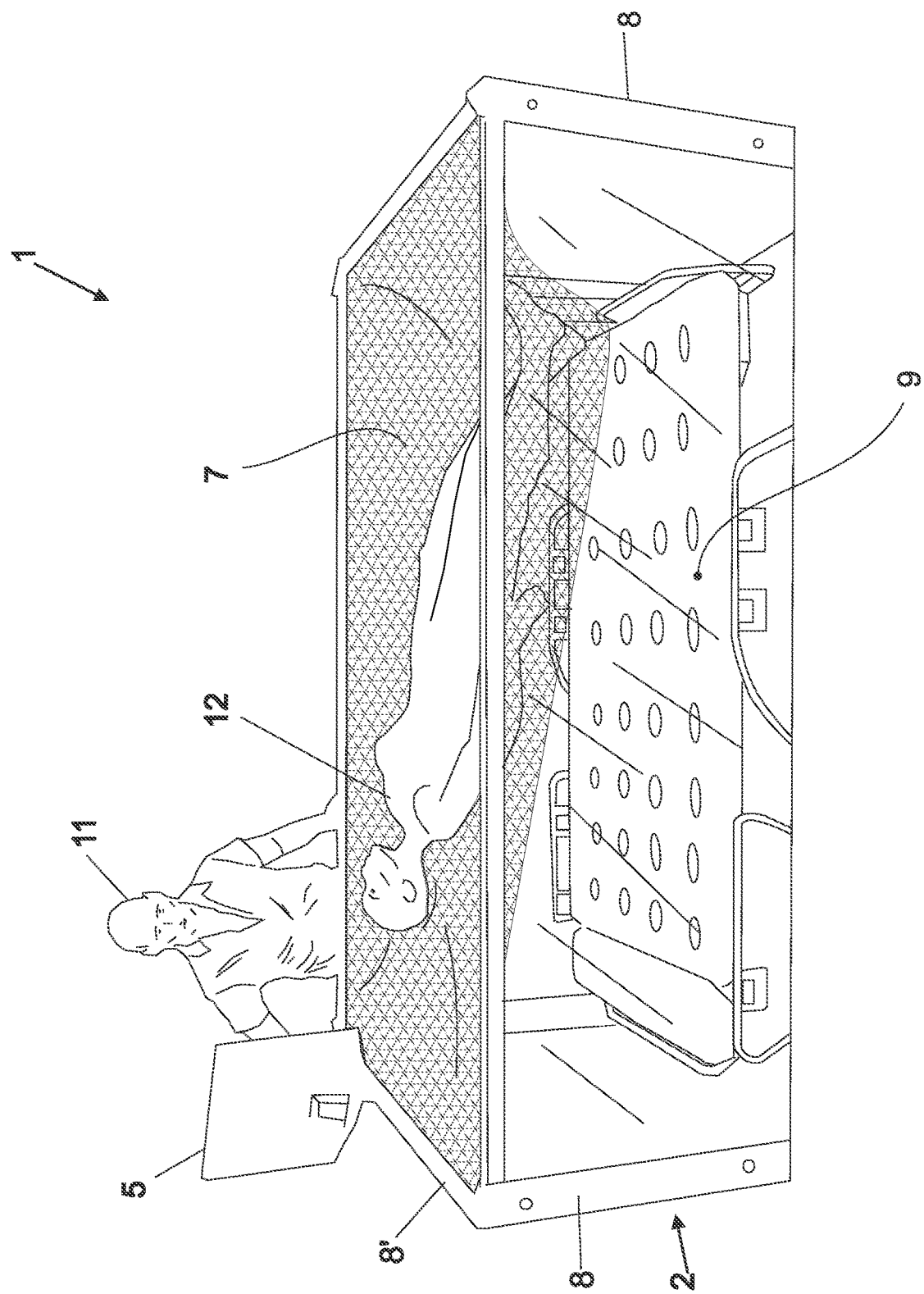

The equipment of the present invention enables pressure application in the cranial caudal direction in a gradual increasing manner. This can be seen in FIGS. 9, 10 and 11. As illustrated, the patient's feet (12) are below the water level while his head remains above the water level, meaning that greater pressure is applied onto the patient's feet than onto his chest. The application of increasing hydrostatic pressure in the cranial caudal direction is important because it displaces the accumulated blood in the peripheral venous system to the central region, with an increase in venous return to the heart and a consequent increase in cardiac output and blood and oxygen supply for the whole organism. By doing so, the main organism changes related to sepsis are corrected, such as arterial hypovolemia, generalized ischemia and hypoxia and delayed microcirculation.

This pressure is easily adjustable, simply and rapidly applied to or directed away from regions such as the chest, neck and head, without impeding or impairing the performance of healthcare professionals in patient care.

Tank (2) comprises an electric heater, a circulating water pump and a digital output thermometer. The three elements together act to precisely control tank (2) water temperature. Alternatively, instead of an electric heater, tank (2) may comprises other means of controlling water temperature, such as gas heaters, and others.

The positive pressure environment is produced by a water tank (2) containing liquid and a membrane (7) that separates the patient (12) from the liquid, allowing for immersion without the patient getting wet (dry immersion). Said membrane presents an area at least 30% greater, when at rest, than the area defined by the horizontal edges (8') of tank (2), allowing for proper patient (12) involvement when immersed in tank (2) and enabling the effect of the Prona position (from the back), without forcing its fixation.

Normally, patient (12) is first accommodated on mattress (14) out of the water and only then is submitted to an intermittent immersion in water.

In a second moment, hydrostatic pressure is applied externally to the patient's body (12) to neutralize the hydrostatic pressure inside the blood capillary, at a pressure value that stops the capillary leak and, at the same time, increases the drainage of the accumulated liquid in the spaces interstitial and cellular, correcting the edema, and increasing lymphatic fluid drainage.

Hydrostatic pressure also compresses dilated peripheral veins and displaces venous blood into the central circulation, increasing venous return to the heart, cardiac output and, consequently, peripheral circulation and tissue oxygenation. For drainage of edema, the hydrostatic pressure applied to blood capillaries must be greater than 15 mmHg and, preferably, greater than the capillary hydrostatic pressure when the edema is too intense. The external pressure to be applied must be inferior than that calculated by subtracting the central venous pressure (VCP) from the mean arterial pressure (MAP): (MAP-VCP), called tissue perfusion pressure.

The dry immersion bed (1) comprises a tank (2) which can be filled with liquid and covered with a waterproof elastic membrane (7) selectively attached to the tank (2) along the horizontal edges (8'), preferably on the outer face of the tank (2), using a gripping device (100).

The gripping devices (100) consist of four metal bars of the same length of the horizontal edges (8'), which are mounted over the horizontal edges (8') or integrated therein (this being the preferred configuration).

Each gripping device (100) comprises: a lever (101); a metal bar in a U-shaped cross-section, hereinafter, "U-bar (110)"; and a metal bar in a rectangular cross-section, hereinafter, "R-bar (102)", housed inside the central cavity of the U-bar (110).

Each gripping device (100) also includes:
i. two galvanized synthetic rubber sheets, at least 3 mm thick each, hereinafter, described as "rubber sheets (104)";
ii. each rubber sheet (104) having a cotton woven fabric (105) attached to its contact surface ("contact surface" meaning the face closest to the membrane (7) during compression of the latter);
iii. at least two pairs of guide pins (103) anchored on the face of the U-bar (110) opposite the lever (101), each of the pairs of guide pins (103) being vertically aligned in bores extending perpendicular to the bottom surface of the U-bar (110) (preferably a plurality of pairs of guide pins (103) are anchored to each of the R-bars).
iv. at least two cylindrical cavities (117) cooperating with the guide pins (103), arranged on the face of the R-Bar (102) proximate to the lever (101) (the face opposite the face of the R-bar (102) to which the rubber sheet or blade (104) is attached);
v. at least one metal spring (108) normally compressed so that it is always pushing the R-bar (102) against the rubber sheets (104) (preferably a plurality of metal springs (108) are employed, all of them centrally aligned in relation to the pairs of guide pins (103), even more preferably some of the springs (108) being concentric to a transmission pin (107));
vi. a linear motion transmission pin, hereinafter transmission pin (107), threaded into the structure of R-bar (102); passing through the structure of U-bar (110) in the portion that extends between the lever (101) and the R-bar (102); which, is pivotably associated with or connected to the axle (113) of the lever (101). The transmission pin (107) comprises a central cylinder body (120), a ring (123) at one of its tips, cooperating with the lever (101) and a threaded tip (122) at the opposite tip; inside the ring (123) there is a graphite bronze sleeve (121).

The lever (101) comprising: an arm (114); a stop (111); a first radius of movement (112); a second radius of movement (109) (said second radius being greater than the first radius (112)); and a central axis (113); all of them being made of machined metal; the lever (101) is assembled and welded after fitting the central axle (113) into the bronze bushing (121), and associating the three distinct parts shown in FIG. 33 (left side of lever (101a), right side of lever (101b) and central axle (113)).

Figure 29A:
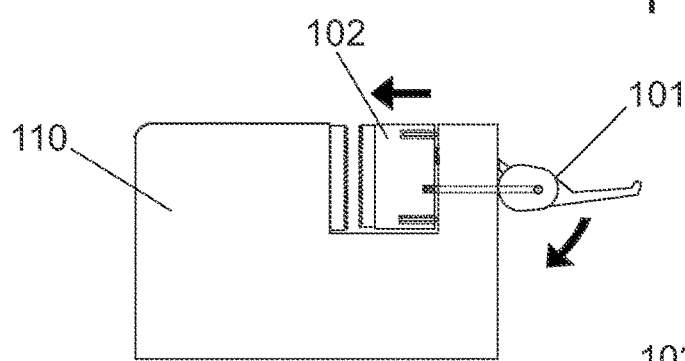
FIG. 29A to 29C are cross-sectional views of the preferred embodiment of the gripping device showing a cam actuator lever in different positions.

The lever (101), operates through a cam action, defined by the fact that the first radius of movement (109) is greater than the second radius of movement (112). The displacement of the lever (101) from the open position of FIG. 29A to the closed position of FIG. 29C allows the transmission pin (107) to penetrate deeper into the U-bar (110), pushing the R-bar (102), which in turn presses the two rubber blades (104) against each other. The stop (111) prevents movement of the lever beyond the open position shown in FIG. 29A.

In other words, the lever (101) is pivoted against the external surface of the U-bar (110), with first and second radii (112) and (109) of movement defining a cam or cam surface; the lever (101) being physically connected to the R-bar (102) by means of the transmission pin (107); the movement of said lever (101) making the R-bar (102) move further away from the lever (101), pressing against one of the inner faces of the U-bar (110), closing a gap between U-bar (110) and R-bar (102).

All of this allows for a high pressure and large contact surface grip, which reduces the stress on the membrane and distributes the pressure through a great surface area of the membrane. The grip also allows an easy installation of the membrane (7), in a way that prevents any damage to the internal or external surface of the membrane (7).

Figure 28:
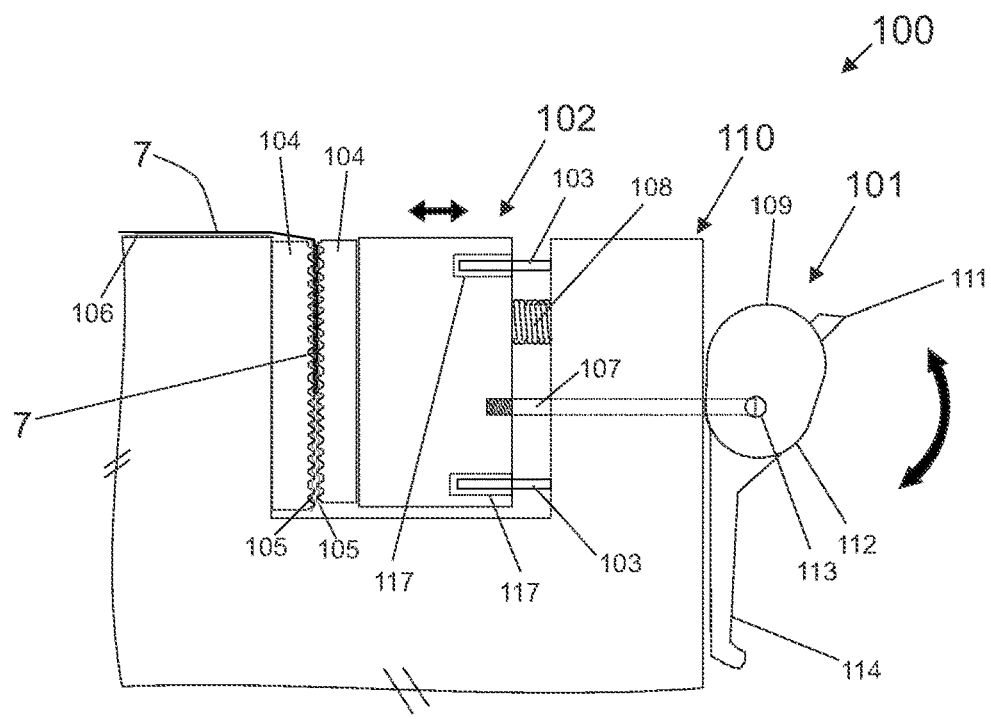

In FIG. 28 it is possible to see the membrane (7) being compressed between the structures of the rubber sheets (104).

The rubber sheets (104) preferably define a corrugated profile on their contact surface, and are covered with a thin cotton fabric (105) that prevents the fusion between the material of the rubber sheets (104) and the membrane (7).

Figure 29B:
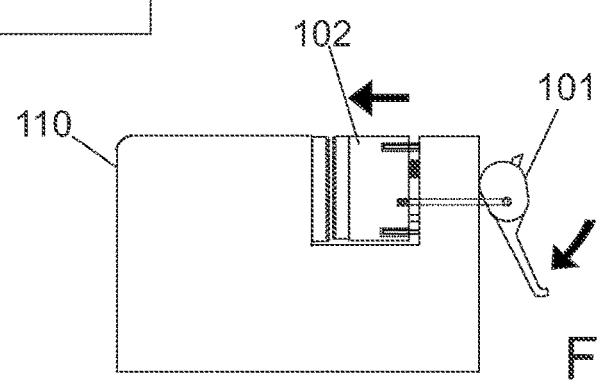
Figure 29C:
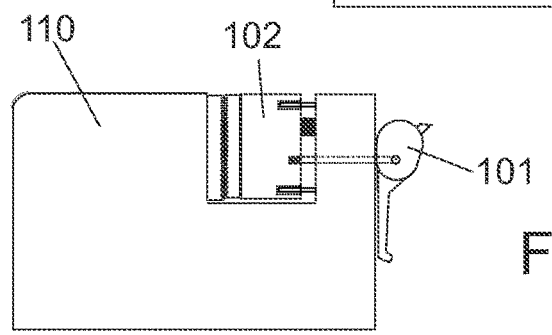

In FIGS. 28 to 29C, surface (106) of U-bar (110), across which membrane (7) extends, is preferably treated with sandblasting and covered with rubberized paint. Surface (106) ends in a rounded profile at the edge of the U-bar (110) defining the largest surface area at the top of the U-bar (110). Its function is to provide an additional grip to the membrane (7), further avoiding the stress and rupture points in the structure of the membrane (7).

Figure 16:
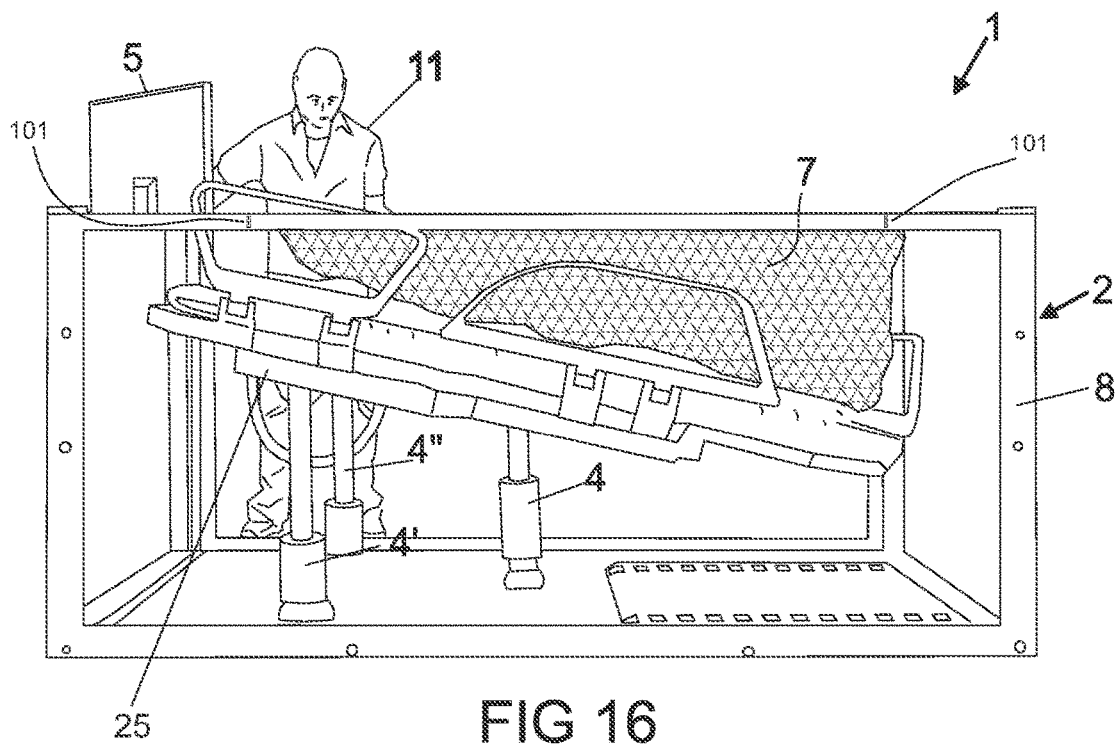
Figure 17:
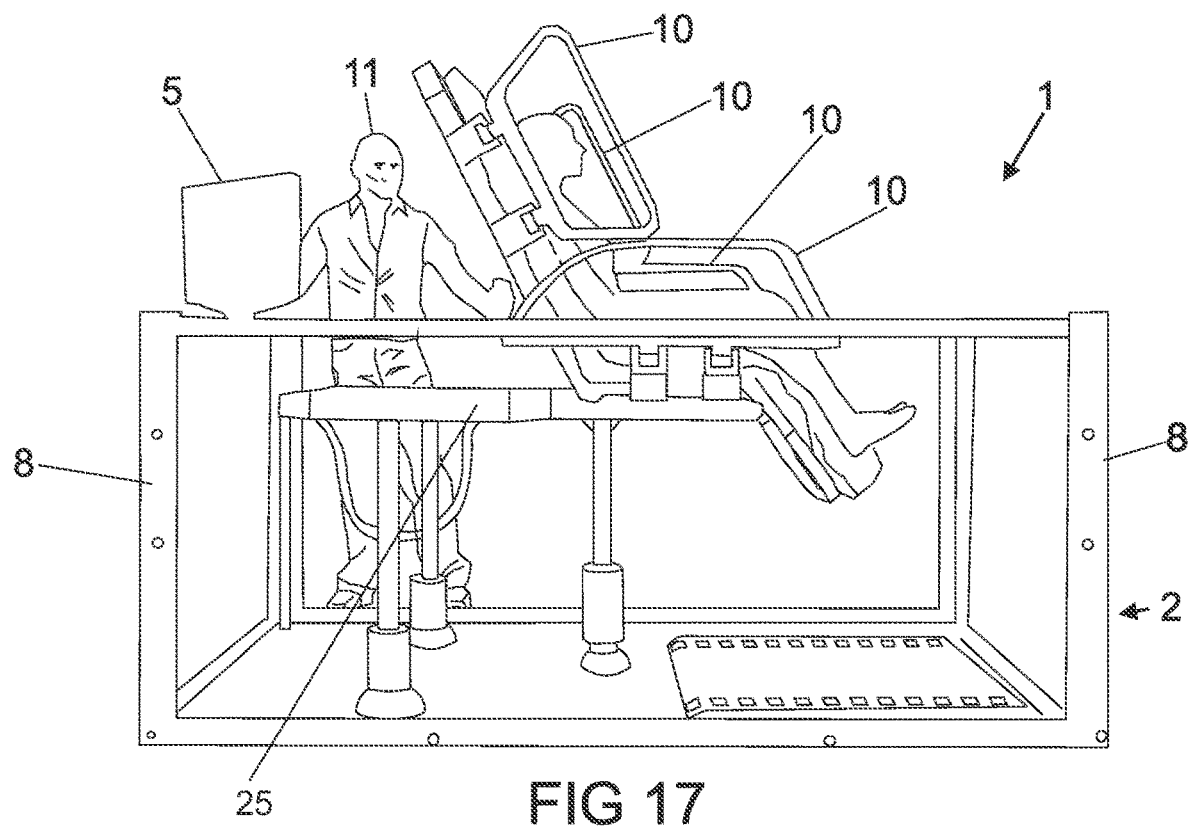
Figure 18:
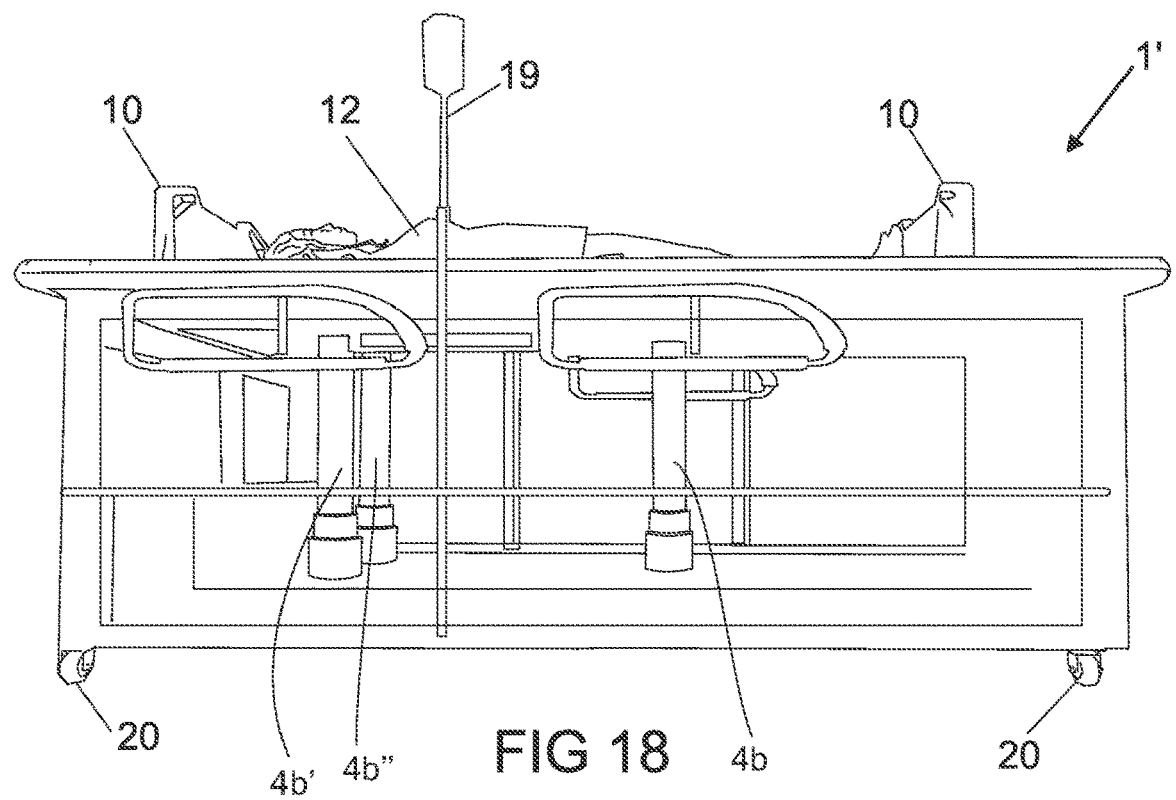
FIGS. 18 to 27 reveal different views for the preferred configuration of the dry immersion bed intended for ICU usage according to the present invention.
Figure 19:
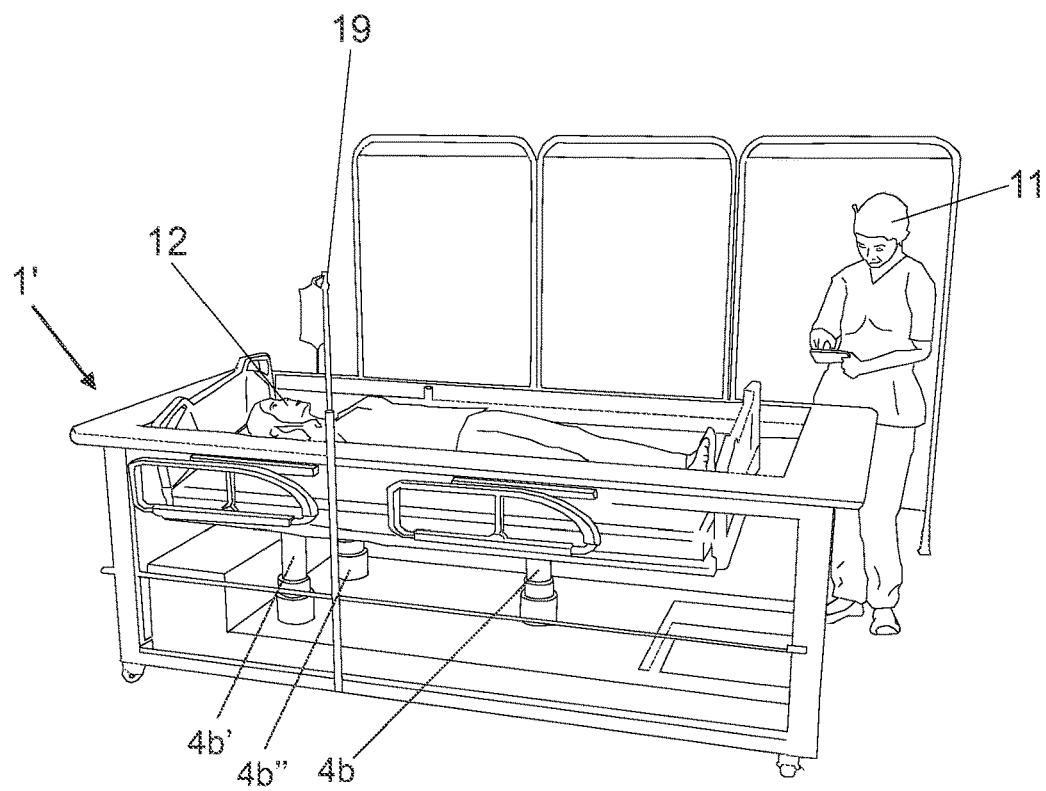

FIG. 30 is a portion extracted from FIG. 16, which shows the arrangement of the levers (101) in relation to the structure of the horizontal tank edges (8').

FIG. 31 shows an alternative configuration in which there is a lid (115) attached by screws (116) to the structure of U-bar (110), providing a shelter to the lever (101). This lid (115) has the function of preventing accidental release of the membrane (7).

FIG. 32 reveals details of the transmission pin (107).

FIG. 33 shows the three metal pieces that comprise the lever (101) before assembly.

Figure 34:
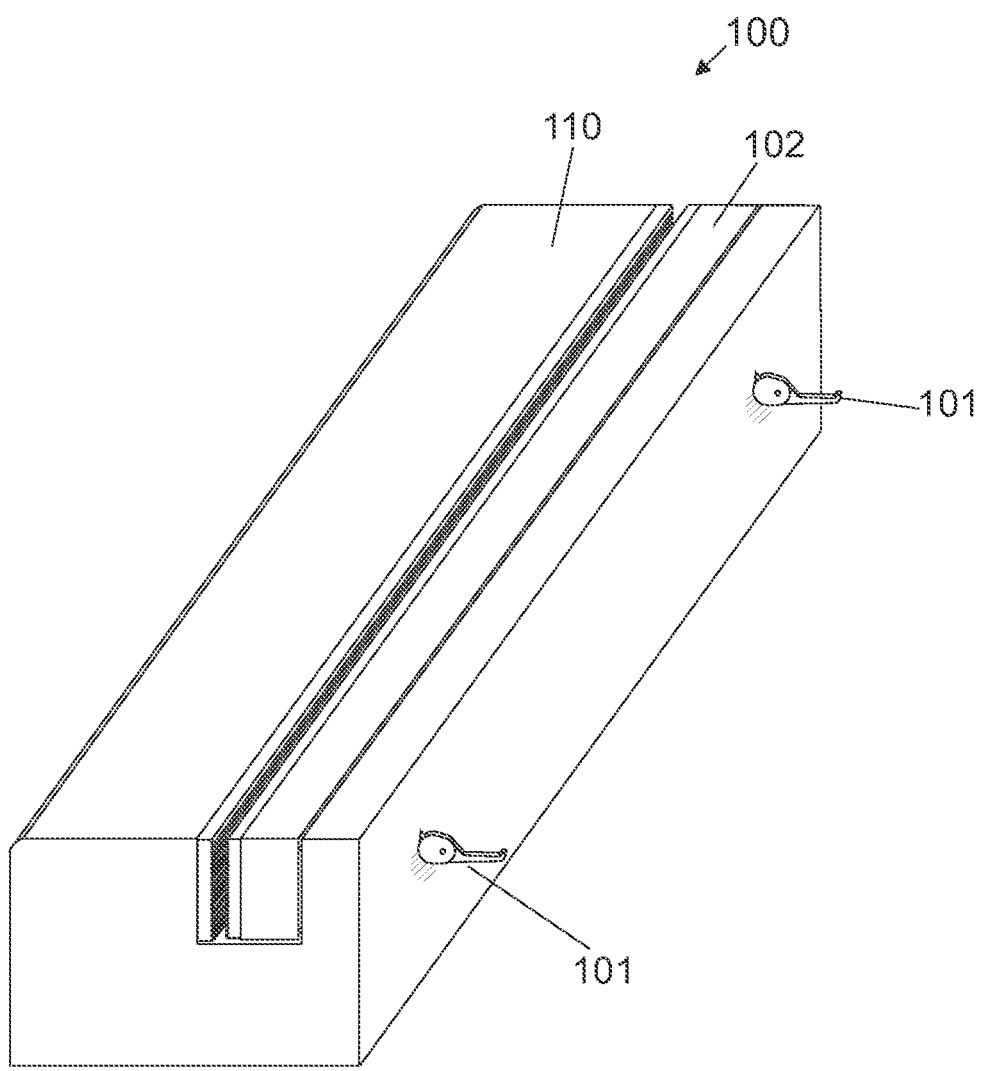

FIG. 34 shows a perspective view of a gripping device (100) in an open arrangement.

Figure 35:
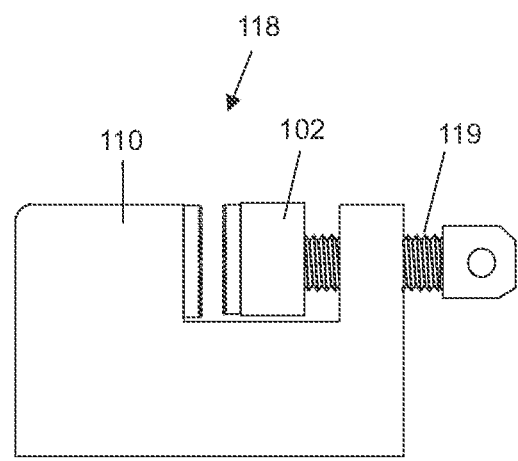

FIG. 35 shows an alternative configuration (118) of the gripping device (100), which consists of a mechanical vise, provided with a rotating screw (119) configured to move the structure of the R-bar (102).

Said membrane (7) covers the entire surface opening defined by the edges (8') of the tank (2), and when using the dry immersion bed (1), it is arranged between the patient (12) and the bed (3).

The membrane (7) is preferably made of a waterproof fabric. Such membrane (7) may comprise two or more main layers. The first layer is preferably a resistant polyester fabric covered by a polyurethane coating, creates a waterproof barrier.

A second embodiment of such membrane is, for instance, a fabric of nylon, covered by polyurethane. In both cases a covering of PVC (Polyvinylchloride) may also be applied as a waterproof protection. An alternative for the covering is a layer of polytetrafluorethylene (PTFE). The thickness of the membrane is less than 1.0 mm, preferable less than 0.5 mm. Other waterproof elastic materials, such as latex or other elastomers may be used to manufacture the membrane. The membrane is attached to the sides of the tank at its upper edges, to a quick-release and frictionless device; in respect to its dimensions, the membrane must have a larger area than the area defined by the tank horizontal edges (8'), at least 30% larger, allowing proper patient involvement during fluid immersion and patient positioning in the PRONA position (from the back), without forcing its fixation to the tank.

With this construction, the membrane (7) is flexible and thin enough to be able to transfer the heat and pressure from the water tank (2) to the patient's skin; wile, at the same time, providing great safety against an undesired rupture.

FIGS. 18 to 27 show a preferred embodiment of the dry immersion bed (1) according to the present invention. Some of the preferred characteristics revealed in these figures are: the metallic support (16), attached to one of the inner faces of the side walls (9""), (9""') and configured to support the hose (13) (see FIG. 27); the tunnel (21) for an X-ray cassette (22), mounted under the backrest segment enabling X-ray image procedures in the sitting position (see FIG. 24); the presence of side rails (10) attached to the side walls external surfaces (see FIGS. 22 and 25); the presence of a mattress (14) with holes; a raised ledge (23), with a rounded external profile, which protrudes out of the limits of the tank (2), emerging from the upper edge of the tank (2) and providing support to the forearms and tools of the health professional (11); among other characteristics perceived by those skilled in the art through the visualization of the drawings and descriptions set forth on this document.

Inside the tank (2) there is the bed (3). The bed (3) is a modified ICU bed, water resistant and equipped with a perforated table or platform arranged under a mattress (14) which may be equipped with holes (15) (in the preferred configuration of the bed (1'), the bed comprises a perforated table or platform, see FIGS. 18 to 27). Said mattress (14), which may be inflated, is preferably attached to the platform using binding strings, in order to be submerged into the water together with the platform, when this element is placed inside the tank (2). Said mattress (14) consists of a material suitable for brackish water, preferably, said mattress is made of elastomer. Preferably, said mattress is filled internally with air or water.

Figure 8:
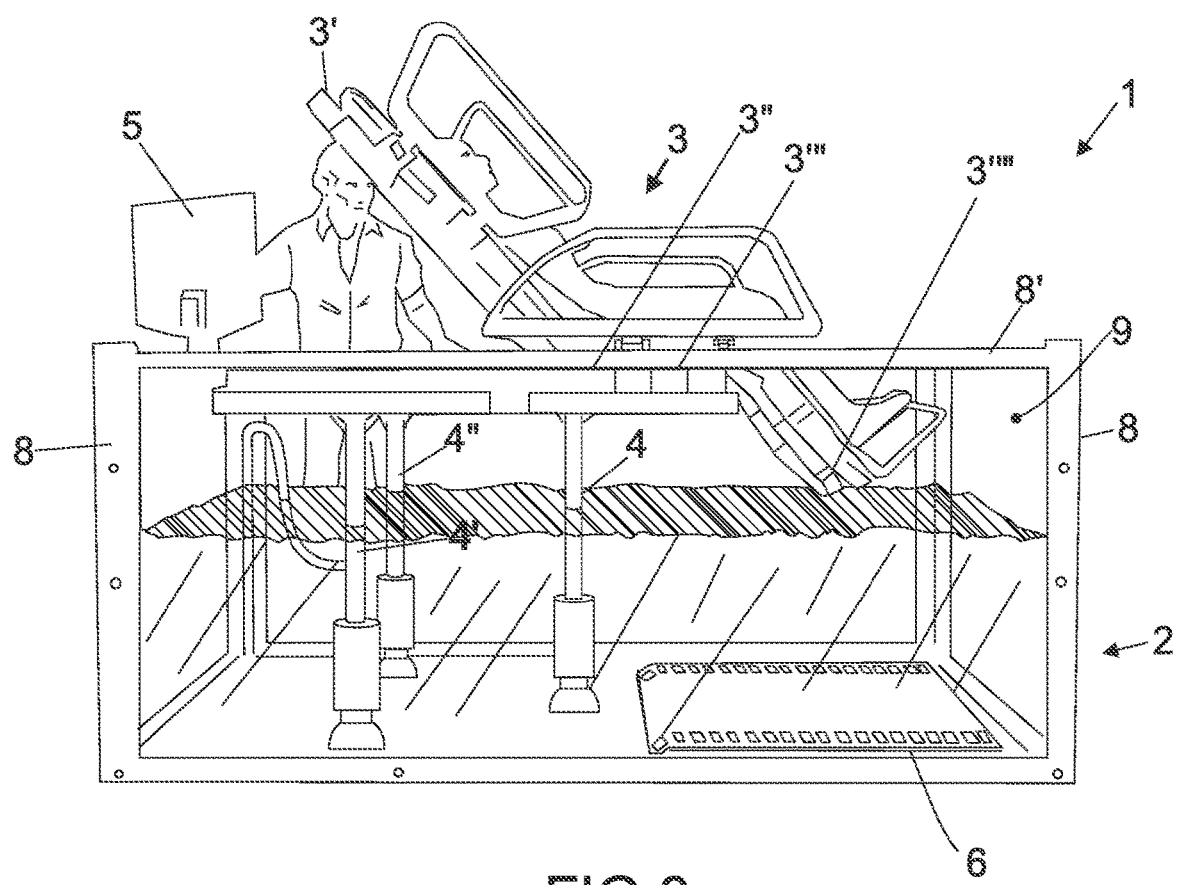

Bed (3) is preferably made of a metal resistant to brackish water and, as best seen in FIG. 8, its platform is segmented into four distinct parts: first platform (3'); second platform (3"); and third platform (3"') and a fourth platform (3""). Between each pair of platforms (first (3') with second (3"), second (3") with third (3"') and third (3"') with fourth (3"")) there is at least one angular actuator (24), configured for relative angular movement between these parts.

This angular actuator (24) consists of a pivotable joint that, in its preferred configuration, comprises a ratchet system to prevent its free rotation and angular movement, requiring a specific force to motivate its angular movement and, consequently, locking the angular position of each platform (3', 3', 3"', 3"') in the desired position.

The first portion (3') is a X-Ray translucent section made up of high pressure laminate. According to one possible configuration of the present invention, the bed (3) is made of the same aluminum alloy commonly used in small marine vessels. The bed (3) also reveals dimensions smaller than the internal dimensions of the tank (2), providing a gap of 1 to 4 cm between its perimeter and the walls (8) of the tank. The bed has two detachable bed ends: head and foot boards.

Figure 1:
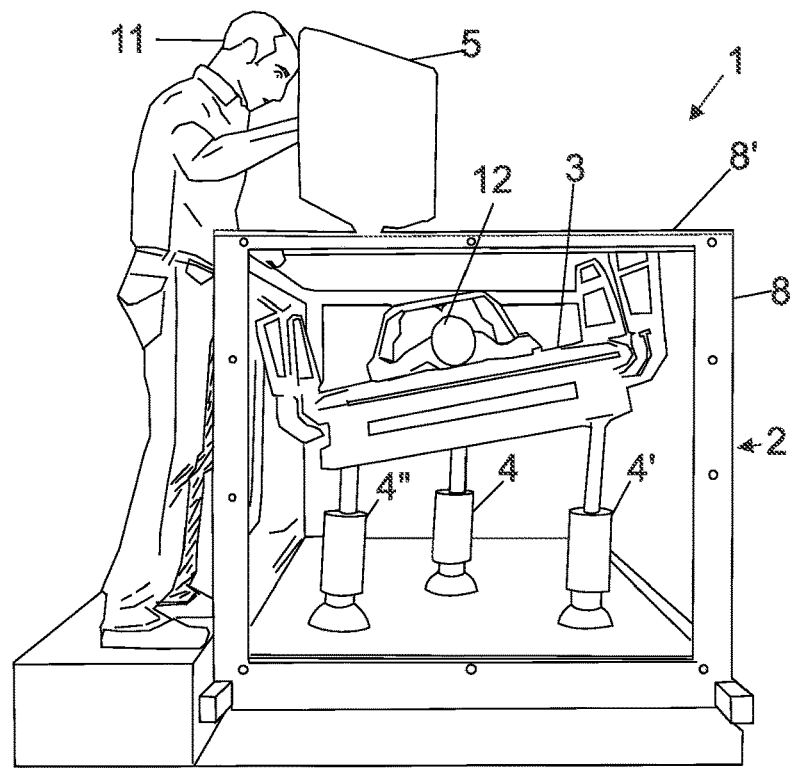
FIGS. 1 to 17 reveal one of the possible configurations proposed for the present invention.
Figure 2:
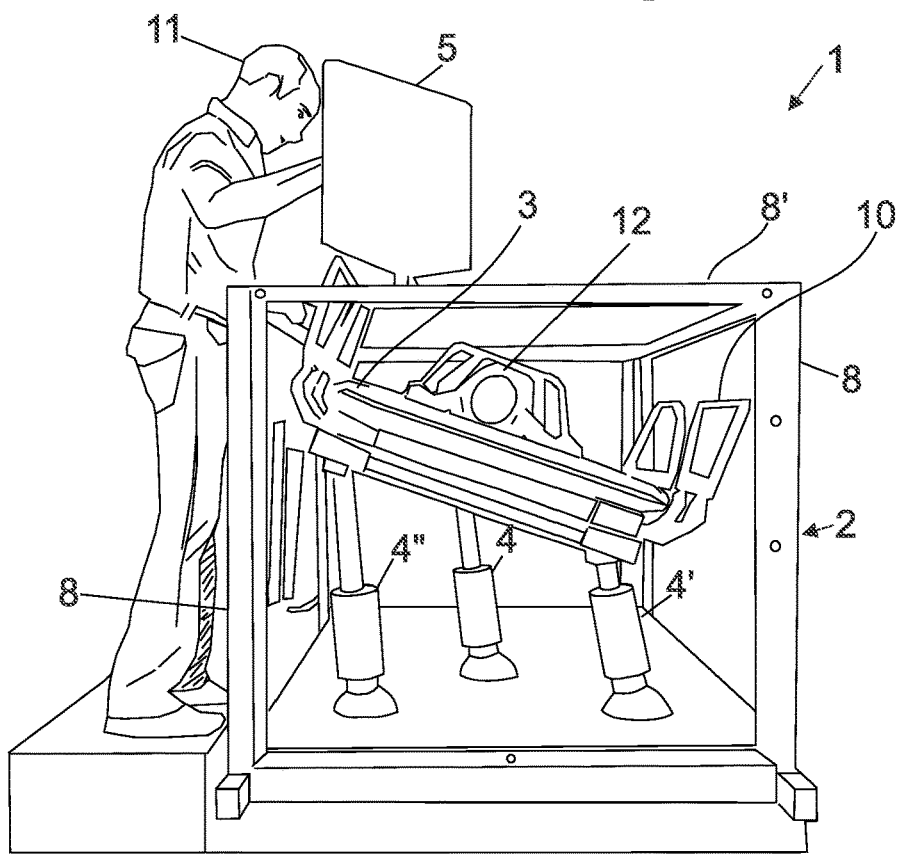
Figure 3:
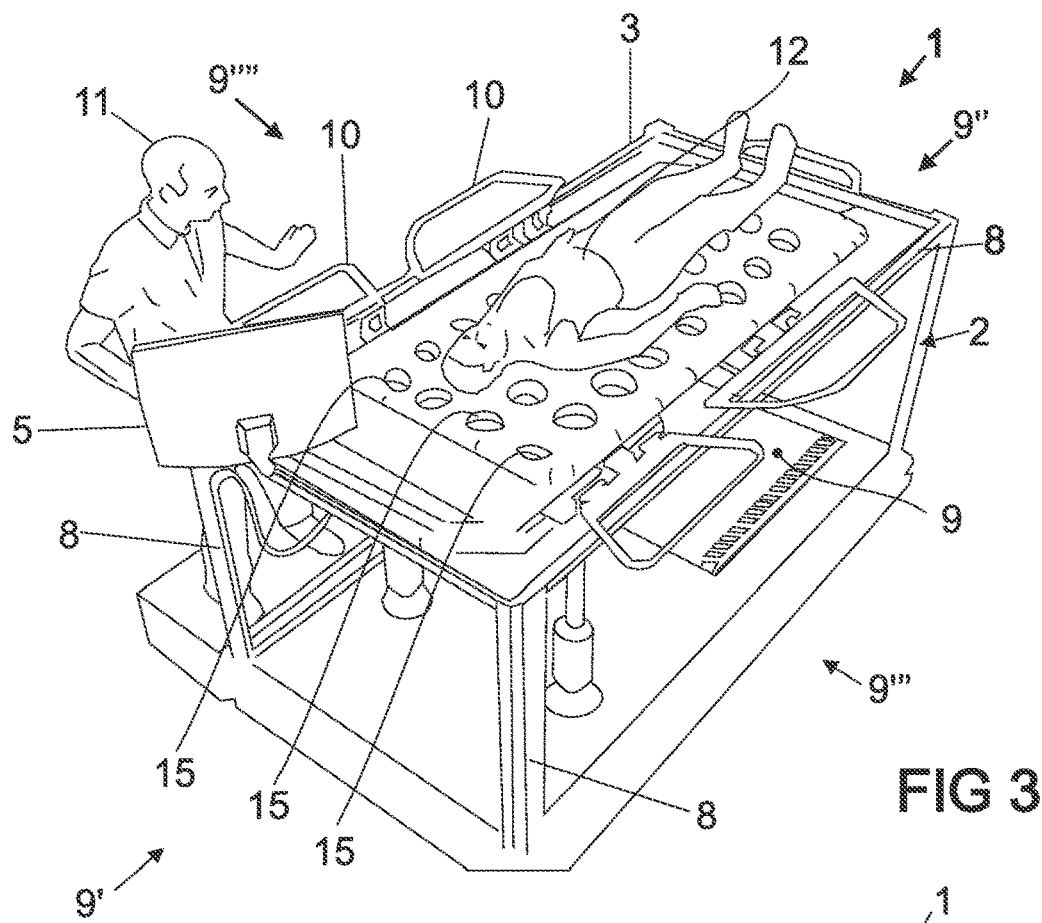
Figure 4:
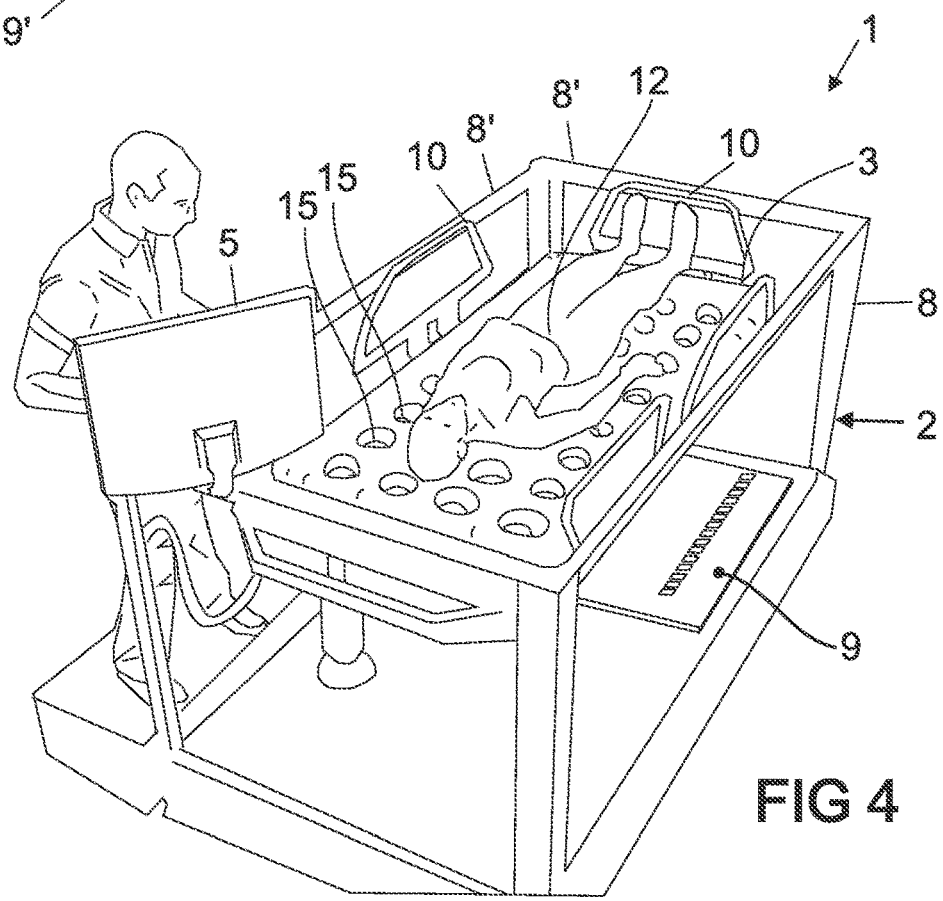
Figure 5:
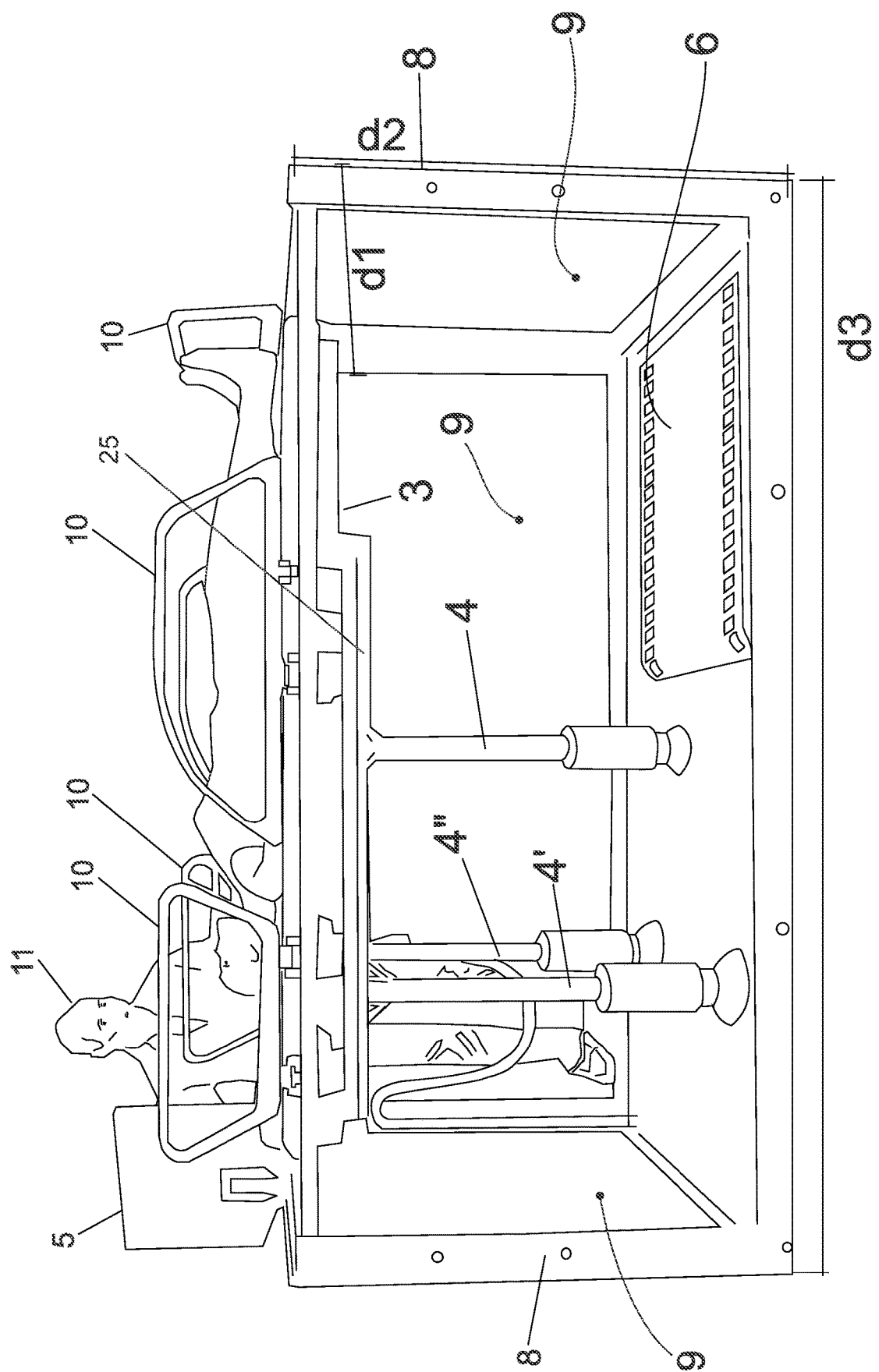
Figure 6:
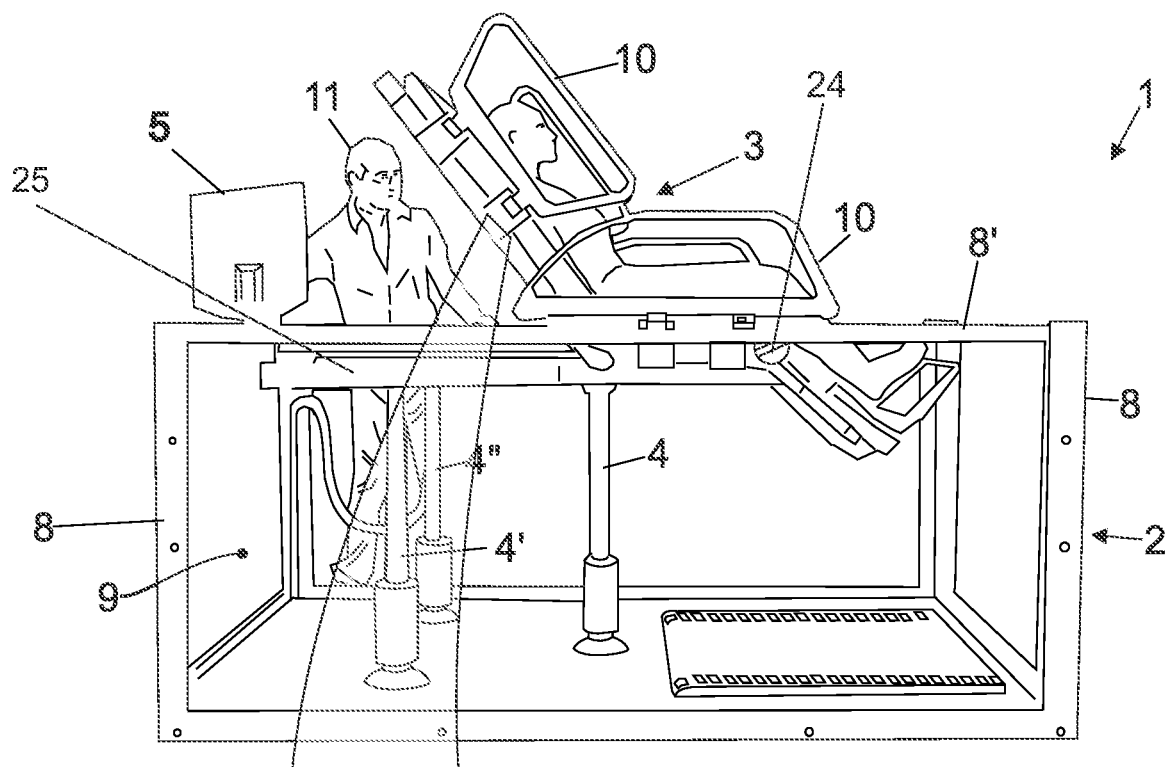
Figure 6A:
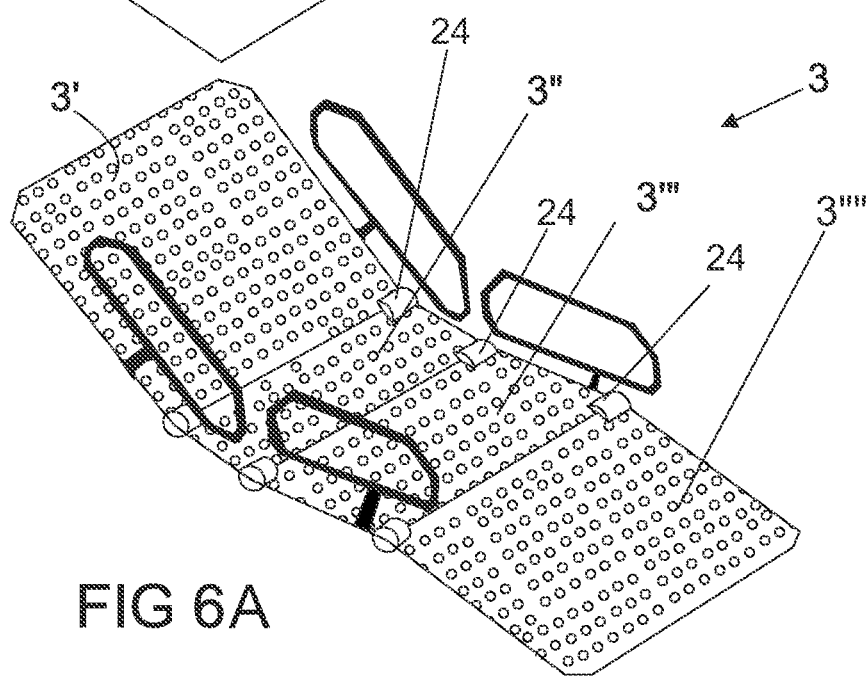
FIG. 6a is an enlarged schematic view of the bed in FIG. 6 with perforated platforms.
Figure 7:
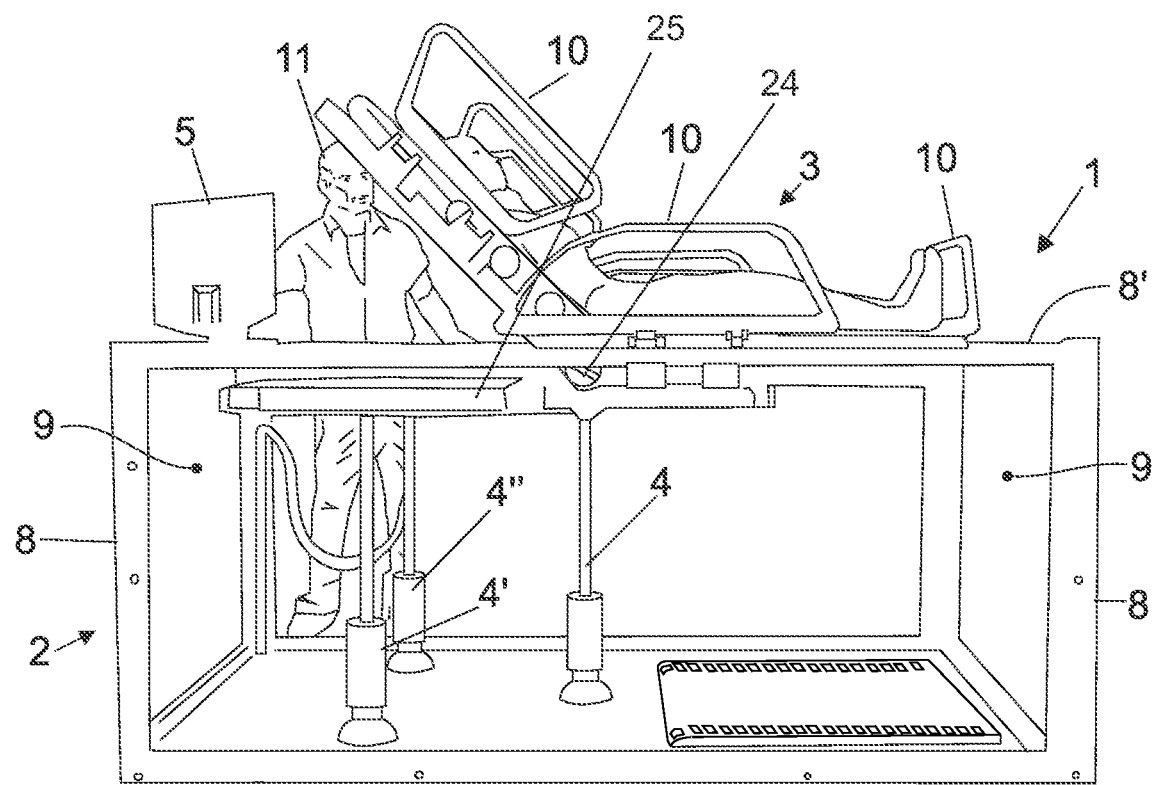

As best seen in FIG. 3, the walls of the tank are divided into front wall (9'); rear wall (9"); right side wall (9"'); left side wall (9""). The rear wall (9") can be temporarily opened to allow maintenance and cleaning of the interior of the tank (2).

The side walls (9'), (9"), (9"') and (9""), see FIG. 3, are made of rigid transparent material such as acrylic or tempered glass. Tempered glass is highly preferred over acrylic due to the fact it is less prone to scratches and surface damages which would impair the view through the tank (2) over the course of time.

The side walls (9'), (9"), (9"') and (9"") are preferably made of laminated tempered glass. This material is suitable for withstanding the significant pressure on the walls due the water column. It also provides a clear view through them. Based on the need of transparency, the dimensions of the tank and the liquid enclosed by it, the side walls (9"') and (9"") will be preferably made of 45 mm of tempered laminated glass. The front wall (9') and rear wall (9") will be preferably made of 15 mm of tempered laminated glass due to their shorter surface area (but they may also comprise a 45 mm width to match the other walls (9"', 9""). The tempered laminated glass comprises layers of tempered glass bonded by a thin membrane of polyvinyl butyral (PVB). An alternative embodiment of it, demands 90 mm of annealed glass for side walls (9"', 9"") and 30 mm of annealed glass for rear and front walls (9', 9").

Figure 20:
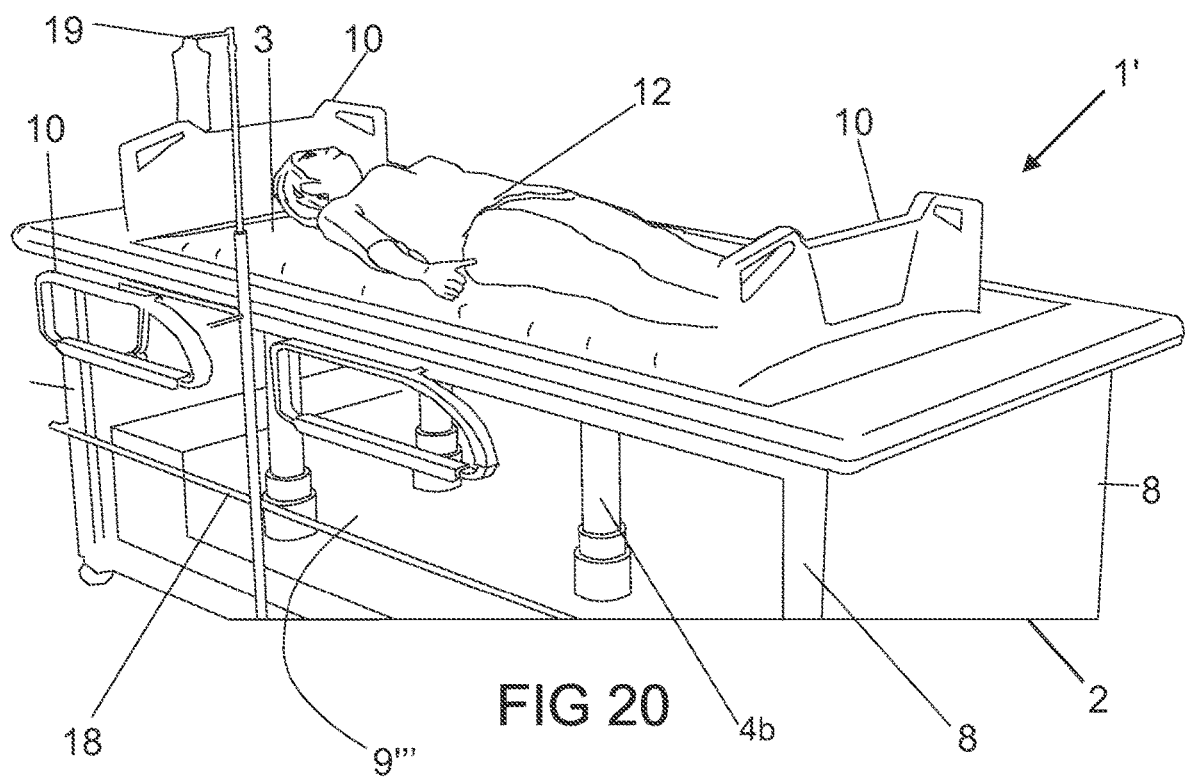
Figure 21:
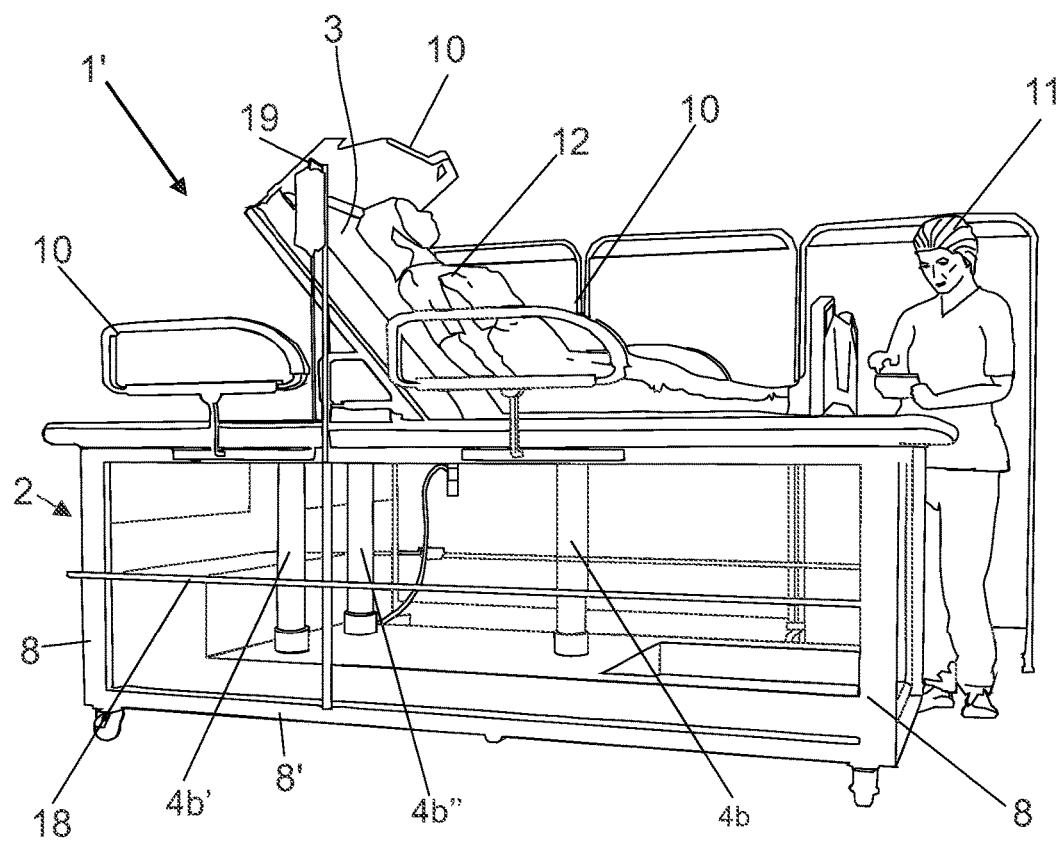
Figure 22:
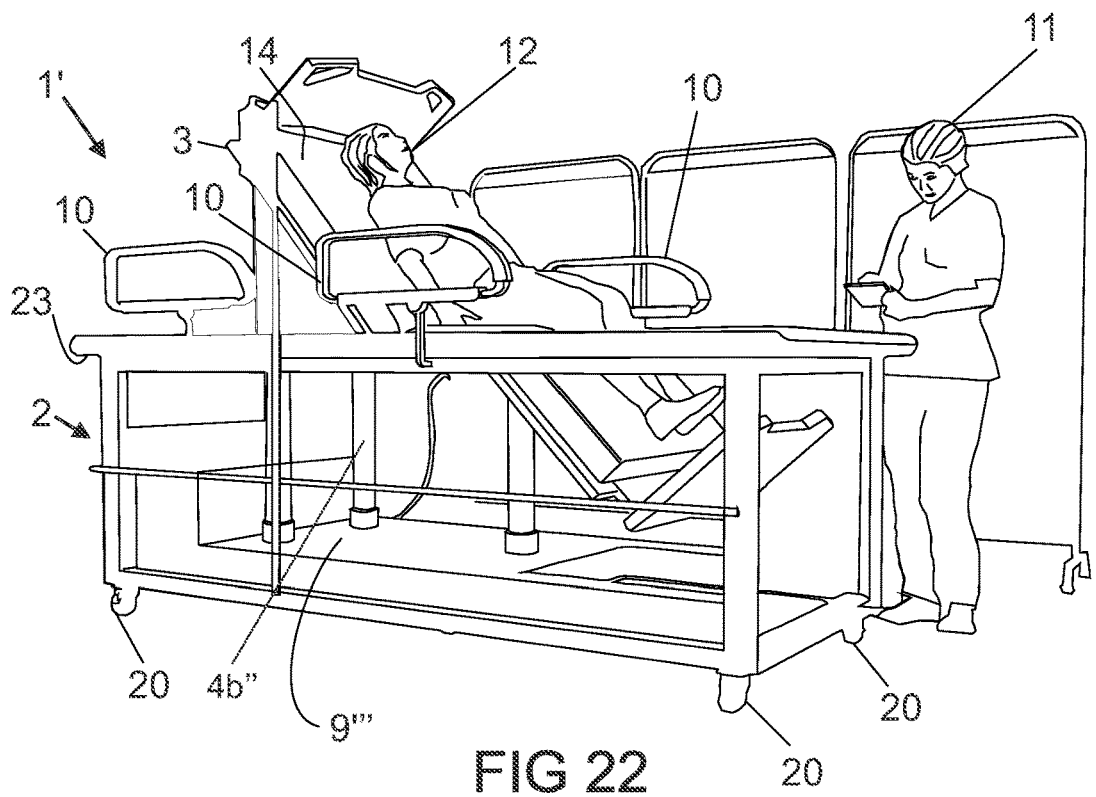
Figure 23:
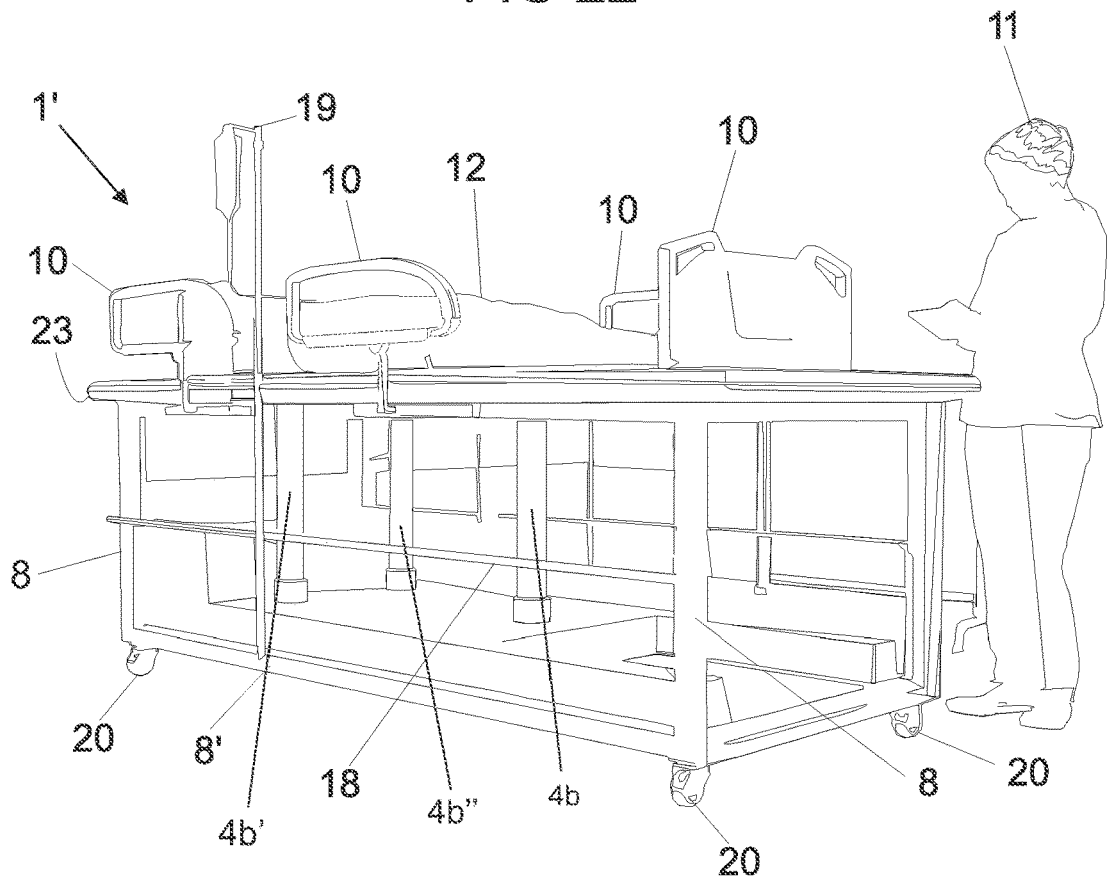
Figure 24:
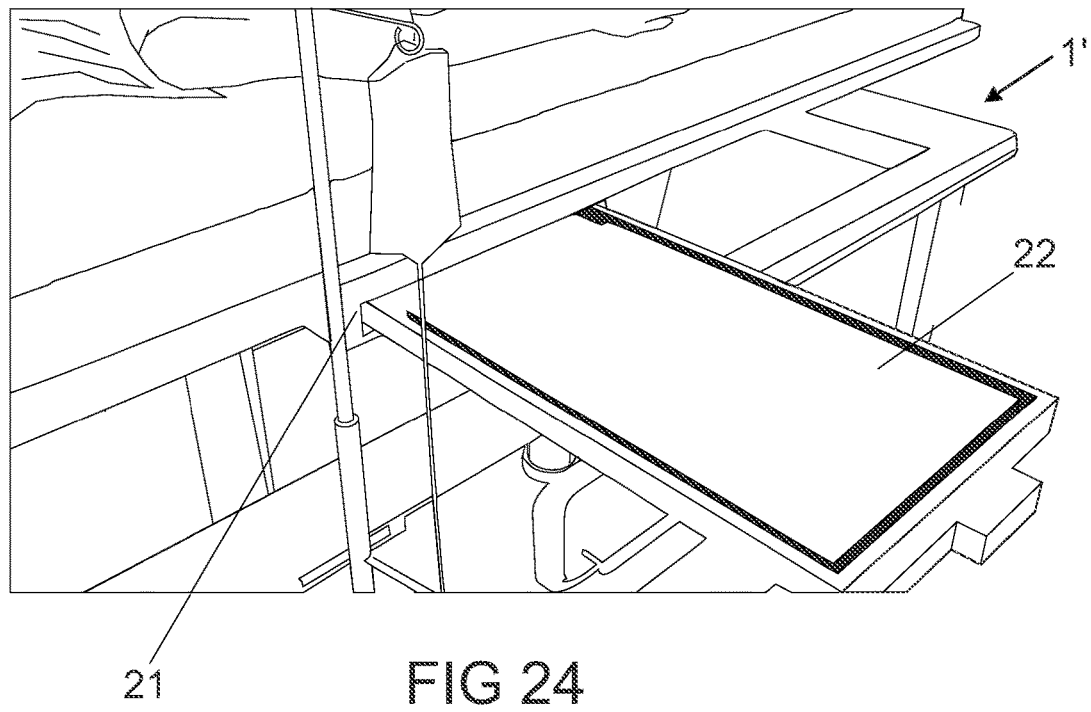
Figure 25:
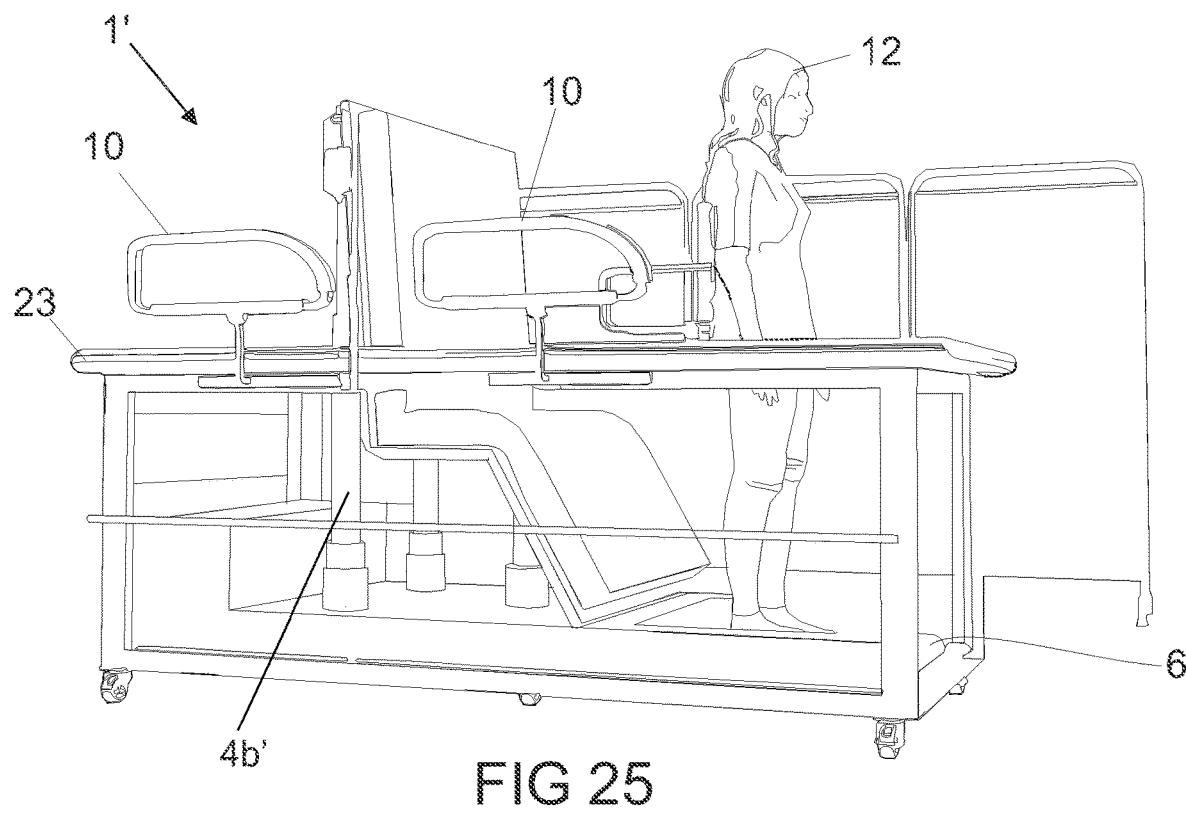
Figure 26:
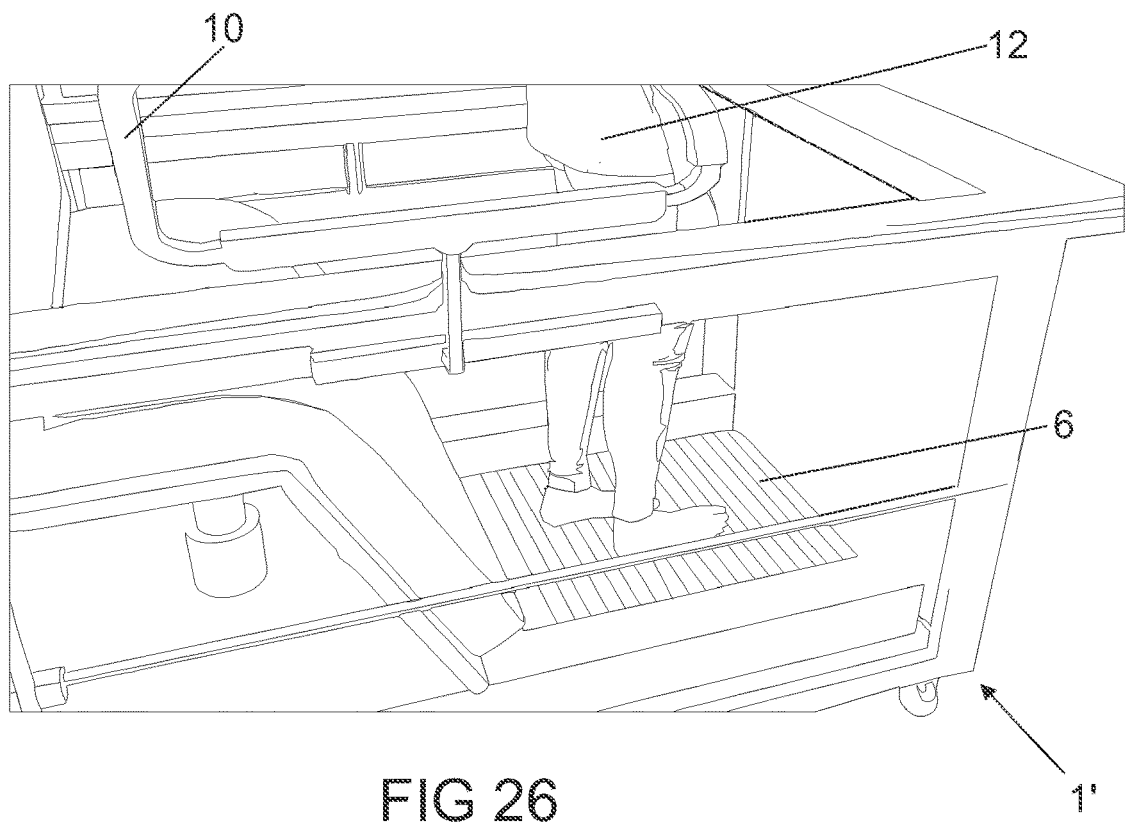

The bed (3) also comprises a panic button to alert nurses and a series of screens or siderails (10), said screens being configured to prevent the patient (12) from falling (12) off of the bed 3. The screens siderails (10) are located on bed (3) the right and left sides of the external lateral walls of the tank and can be lowered to allow patient (12) ingress on the bed or to facilitate access to patient (12) by the healthcare professional (11). Preferably, the side rails (10) are attached to the side walls (9'''), (9''''), at least two on each side, as shown in FIGS. 20 and 21 of this document.

Preferably, the bed (3) also comprises an extender of its fourth portion (3'''), which enables section extension, allowing adaptation for patients over 180 cm in height.

The bed (3) is arranged or supported on at least one actuator, normally three actuators (4), (4'), (4") arranged vertically in relation to the floor of the tank (2). The actuators (4), (4'), (4"), in their preferred configuration, consist of actuators electrically driven by means of a linear electric motor, guaranteeing the use of only electric energy to activate and adjust the position of the bed. Each of the actuators (4), (4'), (4") comprises a linear electric motor, allowing to move and change the position of each of the actuators (4), (4'), (4") individually and, thus, generate the desired bed (3) position.

The linear motors of the actuators, in their preferred configuration, consist of the linear motors described in the patent US 2006/0091762 A1, which basically comprises an electric motor tangentially associated with two spindles. When the electric motor is activated, these spindles are rotated and, consequently, they carry out an expansion or retraction movement of the actuators (4), (4'), (4"), raising and lowering the bed (3) associated with them. The bases of the actuators (4), (4'), (4") are arranged on the tank floor and the three bases together form an isosceles triangle with the peak oriented towards the rear wall (9") and the isosceles base is oriented towards the front wall (9') of the tank (2).

These bases of the actuators (4), (4'), (4") are pivotally fixed to the tank floor, allowing the actuators (4), (4'), (4") to be tilted in relation to the tank floor to position the bed (3) in its desired configuration. In their preferred configuration, the actuator bases also include a seal to prevent the water in the tank from damaging this pivotable fixation.

The end of the actuators (4), (4'), (4") opposite to their bases are fixed to the bottom face of the bed (3) also by means of a pivotable fixation, allowing an inclination of the actuators (4), (4'), (4") in relation to the bed (3) to adjust it to necessary positions according to the actuators (4), (4'), (4") movement.

In their preferred configuration, the end of the actuators (4), (4'), (4") opposite to their bases are associated with an intermediate plate (25), and not directly with the bed (3). This intermediate plate (25) consists of a flat plate, preferably metallic, configured to allow the bed (3), through its own mechanisms, to be adjusted in the desired position even when the actuators (4), (4'), (4") are at their maximum expansion or retraction. Still in its preferred configuration, this intermediate plate (25) comprises a shorter length than the bed (3), allowing the fourth platform not to rest on the intermediate plate (25) thus, it may be folded for greater comfort.

In another configuration of the present invention, the actuators (4b), (4b'), (4b") are hydraulic or pneumatic actuators provided with water sealing means between their moving parts. In this configuration, the dry immersion bed (1) also comprises a hydraulic or pneumatic unit to supply the hydraulic or pneumatic fluid to its actuators (4b), (4b'), (4b"), this hydraulic or pneumatic unit being electrically actuated (see FIGS. 18 to 25).

In yet another configuration, the actuators (4), (4'), (4") can be actuated by pinion and rail system associated with a speed reducer and an electric motor to provide the movement necessary to each actuators (4), (4'), (4").

Preferably, actuators (4), (4'), (4") are resistant to brackish water, containing seals in each movement part to avoid the entrance of water and consequently damage to its components.

As disclosed above the actuators (4), (4'), (4") promote bed (3) upward movement, downward movement, tilting movement and lateral movement, which include all intensive care unit bed (3) movements, even cardiopulmonary resuscitation movements.

The immersion bed (1) is also adapted for carrying out radiological exams and comprises a scale (not shown in the figures) for measuring patient's weigh. Said scale is preferably placed below bed (3), allowing weighing of the patient (12) when the patient is not under immersion. Alternatively, the scale may be located below the tank (2) floor, enabling the patient's weight (12) calculation by weighing the entire tank (2) structure (including water), before and after the patient's entry (12). Another alternative is the addition of an electronic processor in the electronic monitor (5), wherein said processor is able to compute the patient's weight, subtracting the estimated weight of the water inside the tank (calculated based on the water intake flow inside the tank), and the bed's weight (pre-programmed) from the total weight measured for the tank (2).

Tank (2) includes a water temperature control, water treatment system, pump for water circulation system and temperature records system. The equipment also includes water supply and drainage device. Additionally, it contains an electronic monitor (5) configured to display all equipment information, wherein said electronic monitor may be used through a touch-screen interface. In yet another configuration of the present invention, the tank 2 contains an internal device for measuring hydrostatic pressure (barometer) directly associated with the patient's body.

The tank (2) edges (8) and (8') are preferably made of metal, such as stainless steel, with a rectangular shape, and supported by wheels (20) for mobile and static positions. The actuators, frame parts and all the metallic components exposed to water are preferably made of high performance austenitic stainless steel with extremely high PREN (Pitting Resistance Equivalent Number) such as Hastelloy® C-276 or Inconel® Alloy 686. These stainless steels are designed to resist to very harsh conditions, particularly to brackish water. In another possible embodiment the actuators and all metallic components subjected to severe chemical attack is made of super duplex stainless steel, particularly SAF 2507® Alloy 32750. Corrosion resistant steels have high Chrome content what is responsible for forming a passive and stable protective layer on the metal what prevents it from further corrosion. Other high corrosion resistant alloys may also be used for the manufacture of the metallic components. On the tank floor there is a waterproof treadmill (6), configured to provide assistance during patient (12) physiotherapy. The tank (2) is configured to exert a maximum pressure between 15 to at least 74.66 mmHg on the patient's epidermis (12).

Preferred External Bed Dimensions:
Extended Bed Length (d3e): 2389 mm;
Retracted Bed Length (d3r): 2310 mm;
Bed Width (d1): 920 mm;
Bed Height (d2): 1000 mm;
Maximum bed height: 1400 mm;
Preferred Internal Tank Dimensions:
Internal length 2403 mm;
Internal width: 934 mm;

Height: 1000 mm;
External length: 2423 mm;
External width: 954 mm;
External height: 1000 mm.

Alternative dimensions: the same dimensions disclosed above, with a 5% increase or decrease from the preferred embodiment.

Tank's auxiliary feature: it includes supports with hooks (18) for drainage bags on the sides, enabling proper conditions for procedures in ICUs and support for saline-saline bags and venous administrated drugs (19).

Features and Benefits:

Based on the details mentioned above, the dry immersion bed (1) presents the following features and benefits:

(i) enables, when necessary, rapid patient (12) submersion;
(ii) enables, when necessary, immediate or rapid patient (12) removal;
(iii) enables partial patient (12) immersion for a pre-programmed time period determined by the health professional (11);
(iv) enables precise control and accurate measurement of the hydrostatic pressure applied to the patient (12);
(v) enables temperature control in a wide range of values (usually kept at around 35° C.);
(vi) enables cardiopulmonary resuscitation to be performed;
(vii) enables interventions commonly performed in ICUs, such as: deep vein punctures, tracheal intubation, nasogastric and urinary tubes installation, cardiac arrest recovery procedures, tracheostomy, endoscopies, laboratory assays, ultrasound, radiological procedures and others;
(viii) enables patient care without imposing difficulties to the work of health professionals;
(xix) enables viewing of the patient's body (12) even when submerged underwater inside the tank (2), during the day and during the night time;
(xx) enables maintenance of all vital parameters normally measured in an ICU, such as: blood oxygenation, blood pressure, central venous pressure, heartbeat and ECG data;
(xxi) does not pollute the environment around it;
(xxii) does not promote the risk of explosions, radiation emission or any potentially harmful fluids or discharges;
(xxiii) membrane 7 does not cause irritation or allergies to the patient's skin;
(xxiv) enables a homogeneous distribution of hydrostatic pressure throughout the patient's body;
(xxv) enables partial patient immersion without head, neck and thorax to not be immersed under water depending on the conditions of each patient;
(xxvi) it is adapted for use in ICUs, burn recovery centers and recovery centers for anesthetized patients, as well as in homecare, clinics and hospital admissions;
(xxvii) Allows operation in the basic positions of an ICU bed, for example: Fowler, Semi-Fowler, Elevation, Trendelenburg and anti-Trendelenburg position, Cardiac position, plus variations in laterality;
(xxviii) it is easy to handle by the entire medical team and other health professionals;
(xxix) it is accessible and requires easy operational training;
(xxx) enables very quick and easy cleaning;
(xxxi) it is cost effective equipment with cost-compatible manufacturing and maintenance cost according to its benefits;

Cardiac position means: a position that lowers the patient's head and knees (12) by raising the patient's feet (12).

Functions available through the touchscreen of monitor (5):

(i) Function for patient (12) positioning on bed (3) with patient (12) above water level;
(ii) Functions related to diseases: the health professional (11) chooses the disease parameters from a list of options; then he enters the patient data and conditions; the immersion bed (1) then computes this data along with the patient's (12) vital parameters (such as blood pressure) and then determines: the inclination of the bed (3), the patient's (12) immersion depth under water, the relative positioning between the first, second, third and fourth platforms (3'), (3"), (3'''), (3''''), and the water temperature;
(iii) Function related to sepsis treatment: the health professional (11) clicks on the option "sepsis treatment" and bed (3) tilts in order to provide greater pressure in the patient's (12) legs;
(iv) Prone position function: in this position the patient is lying down with his chest down and his back up;
(v) Physiotherapy function on a treadmill: in this function, bed (3) is tilted in the exit position for patient (12) positioning on the treadmill (6), permitting physical rehabilitation exercises;

With regards to the exposed above, the present invention achieves all the objectives that it proposed, revealing a long-sought solution to a problem of great importance worldwide.

Moreover, it is understood that, the bed according to the present invention is also suitable and efficient for the treatment of pathologies such as: edema syndrome (the oedema syndrome), liver cirrhosis, glomerulonephritis; glomerulopathies, hypertonic disease in stages I-II; hypertonic-type neuro-circulatory dystonia; neuroses; degenerative dystrophic diseases of the locomotor system; peptic ulcers, dyskinesia of the gastrointestinal tract; reflective tonic disorders; somatoform dysfunction of the vegetative nervous system; condition after a blood circulation disorder in the brain; ischemic stroke, the consequences of infantile cerebral palsy, including infantile cerebral palsy itself; hypertonic disease; varicose expansion of the veins, stage 1-2; spinal diseases involving neurological symptoms with stages of pain syndrome 1-2; chronic fatigue syndrome; sleep disorders; condition after suffering a myocardial infarction; portal hypertension; condition after alcoholic intoxication—abstinent syndrome, pregnancy, burns, erysipelas, hyperthermia, hypothermia, compartmental syndromes, arterial hypertension.

It should be noted that the scope of protection of this document is limited only to the claim framework, based on its independent claims.

What is claimed is:

1. A dry immersion bed for the treatment of patients, the dry immersion bed comprising: a membrane; a water tank with a floor and four walls, which are a front wall, a rear wall and two side walls; and a bed; wherein said four walls and the floor of the water tank form an open top water-tight container; wherein said membrane is arranged between the patient and the external surface of the bed and fixed to the ends of the upper edges of the tank, separating the patient from a liquid contained in the tank, characterized in that the bed possesses at least the following degrees of freedom in relation to the tank floor:

upward and downward movement in relation to the floor;
forward tilting and backwards tilting in relation to the front wall and rear wall; and
rotation to the right and rotation to the left towards the side walls;

wherein said bed is connected to the tank floor using at least one vertical actuator;

and said bed is segmented into four platforms which are: first platform; second platform; third platform; and fourth platform, wherein said first platform is adapted to support the patient's back and head; the second platform is adapted for the patient's seated support; and the third platform is adapted to support the patient's thigh; and the fourth platform being adapted to support the patient's legs and feet;

wherein said platforms have degrees of freedom between themselves and said bed is equipped with at least three angular actuators, capable of providing a change in the angle defined between the first and second platforms, the second and third platform and between the third and fourth platform respectively;

the at least one vertical actuator together with the angular actuators, enabling the following therapeutic treatment positions: fowler position; semi-fowler position; trendelenburg position; anti-trendelenburg position; cardiac position; anti-shock position; and inclination with head elevation above the patient's feet.

2. The dry immersion bed, according to claim 1 further comprising a treadmill forming part of the tank floor.

3. The dry immersion bed, according to claim 1 wherein the bed comprises rails configured to prevent the patient from falling to the sides of the dry immersion bed.

4. The dry immersion be according to claim 3, wherein the rails are distributed, at least one, at each portion of the bed on both sides of the bed.

5. The dry immersion bed according to claim 3 wherein the rails are attached to side walls of the tank.

6. The dry immersion bed according to claim 1 including a hose for respiratory physiotherapy based on water jets.

7. The dry immersion bed according to claim 1 including means for controlling water temperature.

8. The dry immersion bed according to claim 1 wherein the bed comprises an inflatable mattress.

9. The dry immersion bed according to claim 8 wherein the mattress is equipped with holes capable of allowing water to circulate through its structure.

10. The dry immersion bed according to claim 9 wherein the inflatable mattress is made of elastomer.

11. The dry immersion bed according to claim 1, including a digital monitor disposed outside the tank for displaying vital parameters of the patient, water temperature, bed inclination and function lists of the immersion bed.

12. The dry immersion bed according to claim 11 wherein the following function is displayed on the digital monitor selectively chosen by the health professional: partial immersion pre-programmed time.

13. The dry immersion bed, according to claim 12 further comprising a processor for receiving inputs on: illness, weight, age, blood pressure, central venous pressure, tissue perfusion pressure, hydrostatic pressure and patient height; and wherein said processor analyzes all these inputs and determines a treatment for the patient.

14. The dry immersion bed according to claim 12 further comprising a processor controlling the at least one vertical actuator and the angular actuators to lower the patient's head and knees and simultaneously raise the patient's foot when the health professional inputs a cardio pulmonary resuscitation treatment option into the processor.

15. The dry immersion bed according to claim 11 further comprising a processor controlling the at least one vertical actuator to tilt the bed in order to provide an inclination that promotes greater pressure in the leg region, wherein said pressure decreases towards the patient's abdomen and chest when the health professional inputs a sepsis treatment option into the processor.

16. The dry immersion bed according to claim 1 wherein the membrane comprises a waterproof polyester resistant fabric covered a layer of polyurethane.

17. The dry immersion bed according to claim 16 wherein the membrane presents and area at least 30% greater, when at rest, than the area defined by the horizontal edges.

18. The dry immersion bed according to claim 16 wherein the membrane has a thickness between 0.01-0.5 mm.

19. The dry immersion bed according to claim 1 wherein the membrane is made of nylon fabric covered by polyurethane.

20. The dry immersion bed according to claim 1 wherein the edges are made of stainless steel.

21. The dry immersion bed, according to claim 20 wherein the steel that constitutes the edges is a high performance austenitic stainless steel Hastelloy® C-276 or Inconel® Alloy 686.

22. The dry immersion bed, according to claim 1 wherein the at least one vertical actuator comprises three hydraulic actuators equipped with water sealing means between their moving parts.

23. The dry immersion bed, according to claim 22 wherein the vertical actuators are three electric actuators with water sealing means between their moving parts.

24. The dry immersion bed, according to claim 23, wherein each of the vertical actuators comprise a linear electric motor.

25. The dry immersion bed, according to claim 24, wherein the base of each of the three vertical actuators is attached to the tank floor and the three vertical actuators form an isosceles triangle having a peak oriented towards the rear wall of the tank and a base oriented towards the front wall of the tank.

26. The dry immersion bed according to claim 1 wherein the three hydraulic actuators are made of high performance austenitic stainless steel Hastelloy® C-276 or Inconel® Alloy 686.

27. The dry immersion bed according to claim 1 wherein the tank is configured to exert a maximum pressure between 15 to at least 74.66 mmHg.

28. The dry immersion bed according to claim 1 enabling selective application of pressure in the cranial caudal direction in a gradually increasing and homogeneous manner.

29. The dry immersion bed, according to claim 28 enabling selective application of an increase in cranial pressure of 01 to 74.66 mmHg between the minimum pressure and the pressure maximum effect on the patient.

30. The dry immersion bed according to claim 1 further comprising a device for measuring hydrostatic pressure directly associated with the patient's body.

31. The dry immersion bed, according to claim 1 wherein it comprises four gripping devices for holding the outer edges of the membrane; the four gripping devices consisting of four metal bars with the same length of the horizontal edges, which are mounted over the horizontal edges; each gripping device comprising: at least one lever; one metal bar having a U-shaped cross-section (U-bar); and one metal bar with a rectangular cross-section (R-bar), housed inside the central cavity of the U-bar; wherein the said lever is pivoted at the external surface of the U-bar, with two first radius of movement defining a cam; the lever being physically connected to the R-bar by means of a transmission pin; the movement of said lever making the R-bar move further away from the lever, pressing against one of the inner faces of the U-bar, closing a gap between U-bar and R-bar.

32. The dry immersion bed, according to claim 1, wherein all four walls are made of rigid transparent material.

33. The dry immersion bed, according to claim 32, wherein all four walls are made of acrylic.

34. The dry immersion bed, according to claim 32, wherein all four walls are made of laminated 45 mm tempered glass.

* * * * *